(12) United States Patent
Gary et al.

(10) Patent No.: US 8,324,133 B2
(45) Date of Patent: * Dec. 4, 2012

(54) FUNGICIDE 2-PYRIDYL-METHYLENE-CARBOXAMIDE DERIVATIVES

(75) Inventors: Stéphanie Gary, Lyon (FR); Brian Hill, Camelford (GB); Joseph Perez, Lyon (FR); Rachel Rama, Lyon (FR); Gilbert Spica, Chazay Sur Azegues (FR); Jean-Pierre Vors, Sainte Foy Les Lyon (FR)

(73) Assignee: Bayer Cropscience AG (DE)

( * ) Notice: Subject to any disclaimer, the term of this patent is extended or adjusted under 35 U.S.C. 154(b) by 1308 days.

This patent is subject to a terminal disclaimer.

(21) Appl. No.: 11/919,618

(22) PCT Filed: May 11, 2006

(86) PCT No.: PCT/EP2006/062232
§ 371 (c)(1),
(2), (4) Date: Jan. 11, 2008

(87) PCT Pub. No.: WO2006/120224
PCT Pub. Date: Nov. 16, 2006

(65) Prior Publication Data
US 2010/0010048 A1   Jan. 14, 2010

(30) Foreign Application Priority Data

May 13, 2005 (EP) .................................. 05356079
Aug. 4, 2005 (EP) .................................. 05356130

(51) Int. Cl.
| | | |
|---|---|---|
| *A01N 43/40* | (2006.01) |
| *A01N 37/18* | (2006.01) |
| *C07D 401/00* | (2006.01) |
| *C07D 419/00* | (2006.01) |
| *C07D 417/00* | (2006.01) |
| *C07D 409/00* | (2006.01) |
| *C07D 411/00* | (2006.01) |
| *C07D 405/00* | (2006.01) |
| *C07D 211/70* | (2006.01) |
| *C07D 211/82* | (2006.01) |
| *C07D 213/56* | (2006.01) |

(52) U.S. Cl. ............... 504/130; 504/149; 546/268.4; 546/268.7; 546/276.4; 546/280.4; 546/337; 546/283.4

(58) Field of Classification Search .............. 504/130, 504/149; 546/268.4, 268.7, 276.4, 280.4, 546/283.4, 337
See application file for complete search history.

(56) References Cited

FOREIGN PATENT DOCUMENTS

| | | |
|---|---|---|
| EP | 0 329 020 | 8/1989 |
| EP | 0329020 | 8/1989 |
| WO | WO 99/42447 | 8/1999 |
| WO | WO 01/11966 | 2/2001 |
| WO | WO 02/22583 | 3/2002 |
| WO | WO 2005058833 A1 * | 6/2005 |

* cited by examiner

*Primary Examiner* — Sreeni Padmanabhan
*Assistant Examiner* — Sarah Pihonak
(74) *Attorney, Agent, or Firm* — Ostrolenk Faber LLP

(57) ABSTRACT

The present invention relates to 2-pyridyl-methylene-carboxamide derivatives of formula (I) in which the substituents are as in the description, their process of preparation, their use as fungicide active agents, particularly in the form of fungicide compositions, and methods for the control of phytopathogenic fungi, notably of plants, using these compounds or compositions:

(I)

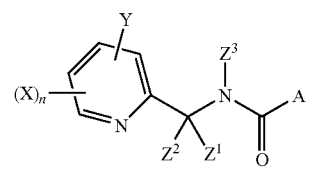

18 Claims, No Drawings

FUNGICIDE 2-PYRIDYL-METHYLENE-CARBOXAMIDE DERIVATIVES

CROSS-REFERENCE TO RELATED APPLICATION(S)

The present application is a 35 U.S.C. §371 national phase conversion of PCT/EP2006/062232 filed 11 May 2006, which claims priority of European Application No. 05356079.3 filed 13 May 2005 and European Application No. 05356130.4 filed 4 Aug. 2005.

The present invention relates to 2-pyridyl-methylene-carboxamide derivatives, their process of preparation, their use as fungicide active agents, particularly in the form of fungicide compositions, and methods for the control of phytopathogenic fungi, notably of plants, using these compounds or compositions.

In international patent application WO-01/11966 certain 2-pyridyl-methylene-carboxamide derivatives are generically embraced in a broad disclosure of numerous compounds. However, this document does not specifically disclose nor suggest to select such compounds wherein the nitrogen atom of the carboxamide residue might be substituted by a cycloalkyl.

In international patent application WO02/22583 discloses certain nitrogen-containing derivatives.

However, this document does not disclose nor suggest that such compounds substituted by 5 membered heterocyclyl groups and wherein the nitrogen atom might be substituted by a cycloalkyl could present a biological activity. In addition, the compounds that are disclosed by this document are systematically substituted by two A and B pyridinyl groups.

It is always of high-interest in agriculture to use novel pesticide compounds in order to avoid or to control the development of resistant strains to the active ingredients. It is also of high-interest to use novel compounds being more active than those already known, with the aim of decreasing the amounts of active compound to be used, whilst at the same time maintaining an effectiveness at least equivalent to the already known compounds.

We have now found a new family of compounds which possess the above mentioned effects or advantages.

Accordingly, the present invention provides 2-pyridyl-methylene-arboxamide derivatives of formula (I):

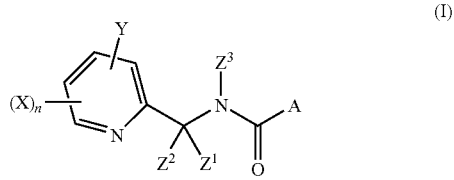

(I)

wherein
A represents a substituted or non substituted 5-membered heterocyclyl group linked to the carbonyl through a carbon atom;
$Z^1$ and $Z^2$, which can be the same or different, represent a hydrogen atom; $C_1$-$C_5$-alkyl; $C_1$-$C_5$-alkenyl; $C_2$-$C_5$-alkynyl; cyano; nitro; a halogen atom; $C_2$-$C_5$-alkoxy; $C_1$-$C_5$-alkenyloxy; $C_2$-$C_5$-alkynyloxy; $C_3$-$C_5$-cycloalkyl; $C_1$-$C_5$-alkylsulphenyl; an amino; $C_1$-$C_5$-alkylamino; di-$C_1$-$C_5$-alkylamino; $C_1$-$C_5$-alkoxycarbonyl; $C_1$-$C_8$-alkylcarbamoyl; di-$C_1$-$C_5$-alkylcarbamoyl; N—$C_1$-$C_5$-alkyl-$C_1$-$C_5$-alkoxycarbamoyl; or
$Z^1$ and $Z^2$ together with the carbon atom to which they are bonded can form a 3-, 4-, 5- or 6 membered carbo- or heterocyclic ring, which can be substituted;
$Z^3$ represents a substituted or non substituted $C_3$-$C_7$ cycloalkyl;
Y represents a $C_1$-$C_5$-halogenalkyl comprising up to 5 halogen atoms which can be the same or different;
X, which can be the same or different, represents a halogen atom; nitro; cyano; hydroxyl; a carboxyl group; $C_1$-$C_8$-alkyl; $C_1$-$C_6$-halogenalkyl comprising up to 5 halogen atoms which can be the same or different; $C_1$-$C_8$-alkylamino; di-$C_1$-$C_8$-alkylamino; $C_1$-$C_8$-alkoxy; $C_1$-$C_6$-halogenoalkoxy comprising up to 5 halogen atoms which can be the same or different; $C_1$-$C_8$-alkylthio; $C_1$-$C_6$-halogenoalkylthio comprising up to 5 halogen atoms which can be the same or different; $C_2$-$C_8$-alkenyloxy; $C_1$-$C_8$-halogenoalkenyloxy comprising up to 5 halogen atoms which can be the same or different; $C_1$-$C_8$-alkenyloxy; Q-$C_8$-halogenoalkinyloxy comprising up to 5 halogen atoms which can be the same or different; $C_1$-$C_8$-cycloalkyl; $C_1$-$C_8$-alkoxycarbonyl; $C_1$-$C_8$-alkylsulphinyl; $C_1$-$C_8$-alkylsulphonyl; $C_1$-$C_8$-halogenoalkylsulphinyl comprising up to 5 halogen atoms which can be the same or different; $C_1$-$C_8$-halogenoalkylsulphonyl comprising up to 5 halogen atoms which can be the same or different or $C_1$-$C_8$-alkoximino-$C_1$-$C_8$-alkyl;
n=0, 1, 2 or 3;
as well as salts; N-oxydes, metallic complexes, metalloidic complexes and optically active isomers thereof.

Any of the compounds according to the invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions), and to the mixtures of all the possible stereoisomers, in all proportions. The diastereoisomers and/or the optical isomers can be separated according to the methods which are known per se by the man ordinary skilled in the art.

Any of the compounds according to the invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

For the compounds according to the invention, halogen means either one of fluorine, bromine, chlorine or iodine and heteroatom can be nitrogen, oxygen or sulfur.

Preferred compounds of formula (I) according to the invention are those in which represents $Z^3$ is not substituted, in particular cyclopropyl.

Other preferred compounds of formula (I) according to the invention are those in which A is selected in the list consisting of:

a heterocycle of formula (A¹)

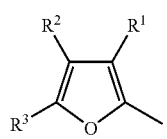

wherein:
$R^1$ to $R^3$ which can be the same or different represent a hydrogen atom; a halogen atom; $C_1$-$C_5$-alkyl or $C_1$-$C_5$-halogenoalkyl comprising up to 5 halogen atoms which can be the same or different;

a heterocycle of formula (A²)

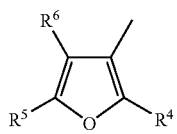

wherein:
$R^4$ to $R^6$ which can be the same or different represent a hydrogen atom; a halogen atom; $C_1$-$C_5$-alkyl or $C_1$-$C_5$-halogenoalkyl comprising up to 5 halogen atoms which can be the same or different;

a heterocycle of formula (A³)

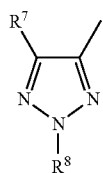

wherein:
$R^7$ represents a hydrogen atom; a halogen atom; $C_1$-$C_5$-alkyl or $C_1$-$C_5$-halogenoalkyl comprising up to 5 halogen atoms which can be the same or different;
$R^8$ represents a hydrogen atom; $C_1$-$C_5$-alkyl or a phenyl substituted by a halogen atom or by a $C_1$-$C_5$-alkyl;

a heterocycle of formula (A⁴)

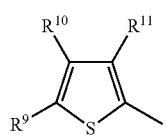

wherein:
$R^9$ to $R^{11}$ which can be the same or different represent a hydrogen atom; a halogen atom; $C_1$-$C_5$-alkyl; an amino; $C_1$-$C_5$-alkoxy; $C_1$-$C_5$-alkylthio or $C_1$-$C_5$-halogenoalkyl comprising up to 5 halogen atoms which can be the same or different;

a heterocycle of formula (A⁵)

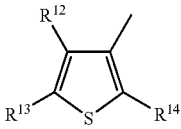

wherein:
$R^{12}$ and $R^{13}$ which can be the same or different represent a hydrogen atom; a halogen atom; $C_1$-$C_5$-alkyl; $C_1$-$C_5$-alkoxy; an amino or $C_1$-$C_5$-halogenoalkyl comprising up to 5 halogen atoms which can be the same or different $R^{14}$ represents a hydrogen atom; a halogen atom; $C_1$-$C_5$-alkyl; an amino or $C_1$-$C_5$-halogenoalkyl comprising up to 5 halogen atoms which can be the same or different;

a heterocycle of formula (A⁶)

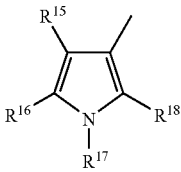

wherein:
$R^{15}$ represents a hydrogen atom; a halogen atom; a cyano; $C_1$-$C_5$-alkyl or $C_1$-$C_5$-halogenoalkyl comprising up to 5 halogen atoms which can be the same or different;

$R^{16}$ and $R^{18}$ which can be the same or different represent a hydrogen atom; a halogen atom; $C_1$-$C_5$-alkoxycarbonyl; $C_1$-$C_5$-alkyl or $C_1$-$C_5$-halogenoalkyl comprising up to 5 halogen atoms which can be the same or different;

$R^{17}$ represent a hydrogen atom or q-$C_5$-alkyl; $C_1$-$C_5$-halogenoalkyl comprising up to 5 halogen atoms which can be the same or different or a phenyl substituted by a halogen atom or by a $C_1$-$C_5$-alkyl;

a heterocycle of formula (A⁷)

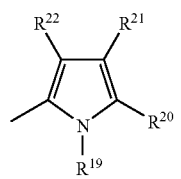

wherein:
$R^{19}$ represents a hydrogen atom; $C_1$-$C_5$-alkyl or a phenyl substituted by a halogen atom or by a $C_1$-$C_5$-alkyl;
$R^{20}$ to $R^{22}$ which can be the same or different represent a hydrogen atom; a halogen atom; $C_1$-$C_5$-alkyl or $C_1$-$C_5$-halogenoalkyl comprising up to 5 halogen atoms which can be the same or different a heterocycle of formula (A⁸)

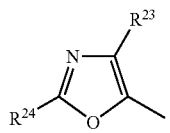

wherein:
$R^{23}$ represents a hydrogen atom; a halogen atom; $C_1$-$C_5$-alkyl; $C_1$-$C_5$-halogenoalkyl comprising up to 5 halogen atoms which can be the same or different;
$R^{24}$ represents a hydrogen atom or $C_1$-$C_5$-alkyl;
    a heterocycle of formula (A⁹)

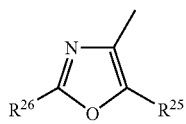

wherein:
$R^{25}$ represents a halogen atom; $C_1$-$C_5$-alkyl or $C_1$-$C_5$-halogenoalkyl comprising up to 5 halogen atoms which can be the same or different;
$R^{26}$ represents a hydrogen atom or $C_1$-$C_5$-alkyl;
    a heterocycle of formula (A¹⁰)

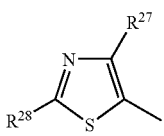

wherein:
$R^{27}$ represents a halogen atom; $C_1$-$C_5$-alkyl or $C_1$-$C_5$-halogenoalkyl comprising up to 5 halogen atoms which can be the same or different;
$R^{28}$ represents a hydrogen atom; a halogen atom; an amino; $C_1$-$C_5$-alkyl; $C_1$-$C_5$-halogenoalkyl comprising up to 5 halogen atoms which can be the same or different or a phenyl substituted by a halogen atom or by a $C_1$-$C_5$-alkyl;
    a heterocycle of formula (A¹¹)

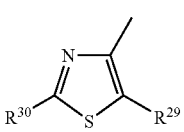

wherein:
$R^{29}$ represents a hydrogen atom; a halogen atom; $C_1$-$C_5$-alkyl or $C_1$-$C_5$-halogenoalkyl comprising up to 5 halogen atoms which can be the same or different;
$R^{30}$ represents a hydrogen atom; a halogen atom; $C_1$-$C_5$-alkyl; $C_1$-$C_5$-halogenoalkyl comprising up to 5 halogen atoms which can be the same or different; an amino; $C_1$-$C_5$-alkylamino; di-$C_1$-$C_5$-alkylamino;

a heterocycle of formula (A¹²)

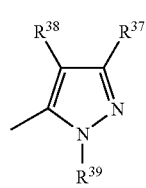

wherein:
$R^{31}$ represents a hydrogen atom; a halogen atom; Q-$C_5$-alkyl or a phenyl substituted by a halogen atom or by a $C_1$-$C_5$-alkyl;
$R^{32}$ represents a hydrogen atom; a halogen atom; $C_1$-$C_5$-alkyl or $C_1$-$C_5$-halogenoalkyl comprising up to 5 halogen atoms which can be the same or different;
$R^{33}$ represents a hydrogen atom; a halogen atom; a nitro or $C_1$-$C_5$-halogenoalkyl comprising up to 5 halogen atoms which can be the same or different;
    a heterocycle of formula (A¹³)

wherein:
$R^{34}$ represents a hydrogen atom; a halogen atom; $C_1$-$C_5$-alkyl; $C_3$-$C_5$-cycloalkyl; $C_1$-$C_5$-halogenoalkyl comprising up to 5 halogen atoms which can be the same or different; $C_1$-$C_5$-alkoxy; $C_1$-$C_5$-alkynyloxy; $C_1$-$C_5$-halogenoalkoxy comprising up to 5 halogen atoms which can be the same or different or a phenyl substituted by a halogen atom or by a $C_1$-$C_5$-alkyl;
$R^{35}$ represents a hydrogen atom; a halogen atom; $C_1$-$C_5$-alkyl; a cyano; $C_1$-$C_5$-alkoxy; $C_1$-$C_5$-alkylthio; $C_1$-$C_5$-halogenoalkyl comprising up to 5 halogen atoms which can be the same or different; $C_4$-$C_5$-halogenoalkoxy comprising up to 5 halogen atoms which can be the same or different; an amino; $C_1$-$C_5$-alkylamino or di($C_1$-$C_5$-alkyl);
$R^{36}$ represents a hydrogen atom; $C_1$-$C_5$-alkyl or a phenyl substituted by a halogen atom or by a $C_1$-$C_5$-alkyl;
    a heterocycle of formula (A¹⁴)

wherein:
$R^{37}$ and $R^{38}$ which can be the same or different represent a hydrogen atom; a halogen atom; $C_1$-$C_5$-alkyl; $C_1$-$C_5$-halogenoalkyl comprising up to 5 halogen atoms which can be the same or different; $C_1$-$C_5$-alkoxy or a $C_1$-$C_5$-alkylthio;
$R^{39}$ represents a hydrogen atom; $C_1$-$C_5$-alkyl or a phenyl substituted by a halogen atom or by a $C_1$-$C_5$-alkyl;

a heterocycle of formula (A$^{15}$)

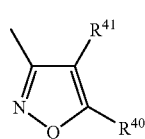

wherein:
R$^{40}$ and R$^{41}$ which can be the same or different represent a hydrogen atom; a halogen atom; C$_1$-C$_5$-alkyl or C$_1$-C$_5$-halogenoalkyl comprising up to 5 halogen atoms which can be the same or different;

a heterocycle of formula (A$^{16}$)

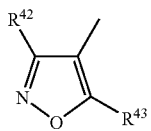

wherein:
R$^{42}$ and R$^{43}$ which can be the same or different represent a hydrogen atom; C$_1$-C$_5$-alkyl; C$_1$-C$_5$-halogenoalkyl comprising up to 5 halogen atoms which can be the same or different; an amino or a phenyl substituted by a halogen atom or by a C$_1$-C$_5$-alkyl;

a heterocycle of formula (A$^{17}$)

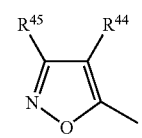

wherein:
R$^{44}$ and R$^{45}$ which can be the same or different represent a hydrogen atom; a halogen atom; C$_1$-C$_5$-alkyl or C$_1$-C$_5$-halogenoalkyl comprising up to 5 halogen atoms which can be the same or different;

a heterocycle of formula (A$^{18}$)

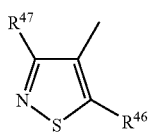

wherein:
R$^{46}$ represents a hydrogen atom; C$_1$-C$_5$-alkyl; C$_1$-C$_5$-halogenoalkyl comprising up to 5 halogen atoms which can be the same or different or C$_1$-C$_5$-alkylsulfanyl;
R$^{47}$ represents a hydrogen atom; a halogen atom or C$_1$-C$_5$-alkyl;

a heterocycle of formula (A$^{19}$)

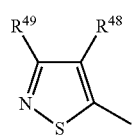

wherein:
R$^{48}$ and R$^{49}$ which can be the same or different represent a hydrogen atom; a halogen atom; C$_1$-C$_5$-alkyl or C$_1$-C$_5$-halogenoalkyl comprising up to 5 halogen atoms which can be the same or different;

a heterocycle of formula (A$^{20}$)

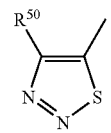

wherein:
R$^{50}$ represents a halogen atom; C$_1$-C$_5$-alkyl or C$_1$-C$_5$-halogenoalkyl comprising up to 5 halogen atoms which can be the same or different.

Heterocycle A$^{13}$ is particularly advantageous as substituent A for the compounds according to the invention.

Some other preferred compounds according to the invention are compounds of formula (I) wherein A represents a 5-membered heterocycle that is substituted in position ortho. Such compounds can also be defined with A representing a a-substituted 5-membered heterocycle.

Still other preferred compounds of formula (I) according to the invention are those in which X, which can be the same or different, represents a halogen atom; C$_1$-C$_8$-alkyl; C$_1$-C$_5$-halogenoalkyl comprising up to 5 halogen atoms which can be the same or different; C$_1$-C$_8$-alkoxy; C$_1$-C$_8$-halogenoalkoxy comprising up to 5 halogen atoms which can be the same or different.

Still other preferred compounds of formula (I) according to the invention are those wherein Y represents trifluoromethyl.

Still other preferred compounds of formula (I) according to the invention are those wherein n is equal to 1.

The above mentioned preferences with regard to the substituents of the compounds according to the invention can be combined in various manners. These combinations of preferred features thus provide sub-classes of compounds according to the invention. Examples of such sub-classes of preferred compounds according to the invention can combine:

preferred features A of with preferred features of Z$^3$;
preferred features A of with preferred features of Y;
preferred features of A with preferred features of X;
preferred features of A with preferred features of n;
preferred features of A with preferred features of Z$^3$ and Y;
preferred features of A with preferred features of Z$^3$ and X;
preferred features of A with preferred features of Z$^3$ and n;
preferred features of A with preferred features of Z$^3$, Y and X;
preferred features of A with preferred features of Z$^3$, Y and n;
preferred features of A with preferred features of Z$^3$, X and n;

preferred features of A with preferred features of $Z^3$, Y, X and n;
preferred features of $Z^3$ with preferred features of Y;
preferred features of $Z^3$ with preferred features of X;
preferred features of $Z^3$ with preferred features of n;
preferred features of $Z^3$ with preferred features of Y and X;
preferred features of $Z^3$ with preferred features of Y and n;
preferred features of $Z^3$ with preferred features of X and n;
preferred features of $Z^3$ with preferred features of Y, X and n;
preferred features of Y with preferred features of X;
preferred features of Y with preferred features of n;
preferred features of Y with preferred features of X and n.

In these combinations of preferred features of the substituents of the compounds according to the invention, the said preferred features can also be selected among the more preferred features of each of $Z^3$ and A so as to form most preferred subclasses of compounds according to the invention.

The present invention also relates to a process for the preparation of compounds of formula (I). Thus according to a further aspect according to the invention, there is provided a process P1 for the preparation of compound of formula (I) and illustrated according to the following reaction scheme:

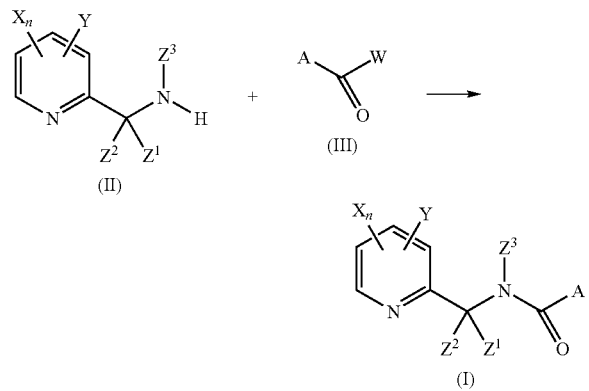

Process P1 in which
A, $Z^1$, $Z^2$, $Z^3$, X, n and Y are as herein-defined;
W represents a halogen atom or hydroxyl.

Process P1 may be performed in the presence of an acid binder and in the presence of a solvent.

Amine derivatives of formula (II) are known or can be prepared by known processes, r example as described in WO-01/11966 pages 20, 21 and 23.

Carboxylic acids, acid chlorides, acid bromides or acid fluorides of formula (III) are known or can be prepared by known processes (WO-93/11117, p 16-20; Nucleosides & Nucleotides, 1987, p 737-759; Bioorg. Med. Chem. Lett., 2002, p 2105-2108).

Suitable acid binders for carrying out process P1 according to the invention can be inorganic and organic bases which are customary for such reactions. Preference is given to using alkaline earth metal or alkali metal hydroxides, such as sodium hydroxide, calcium hydroxide, potassium hydroxide or other ammonium hydroxide derivatives; alkali metal carbonates, such as sodium carbonate, potassium carbonate, potassium bicarbonate, sodium bicarbonate; alkali metal or alkaline earth metal acetates, such as sodium acetate, potassium acetate, calcium acetate; and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

It is also possible to work in the absence of any additional acid binder.

Suitable solvents for carrying out process P1 according to the invention can be customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholane.

When carrying out process P1 according to the invention, the reaction temperatures can be varied within a relatively wide range. In general, these processes are carried out at temperatures from 0° C. to 160° C., preferably from 10° C. to 120° C. A way to control the temperature for the processes according to the invention is to use micro-wave technology.

Process P1 according to the invention is generally carried out under atmospheric pressure. It is also possible to operate under elevated or reduced pressure.

When carrying out process P1 according to the invention, the amine derivative of formula (II) can be employed as its hydrochloric salt.

When carrying out process P1 according to the invention, 1 mol or an excess of the amine derivative of formula (II) or from 1 to 3 mol of acid binder can be employed per mole of acid derivatives (III).

It is also possible to employ the reaction components in other ratios. Work-up is carried out by known methods.

In general, the reaction mixture is concentrated under reduced pressure. The residue that remains can be freed by known methods, such as chromatography or recrystallization, from any impurities that may still be present.

Compounds of formula (I) according to the invention can be prepared according to the herein described processes. It will nevertheless be understood that, on the basis of his general knowledge and of available publications, the skilled worker will be able to adapt these processes according to the specifics of each of the compounds which it is desired to synthesise.

In a further aspect, the present invention also relates to a fungicide composition comprising an effective and non-phytotoxic amount of an active compound of formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be controlled, the type of crop, the climatic conditions and the compounds included in the fungicide composition according to the invention.

This amount can be determined by systematic field trials, which are within the capabilities of a person skilled in the art.

Thus, according to the invention, there is provided a fungicide composition comprising, as an active ingredient, an effective amount of a compound of formula (I) as herein-defined and an agriculturally acceptable support, carrier or filler.

According to the invention, the term "support" denotes a natural or synthetic, organic or inorganic compound with which the active compound of formula (I) is combined or associated to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition according to the invention may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the present compounds containing sulphate, sulphonate and phosphate functions. The presence of at least one surfactant is generally essential when the active compound and/or the inert support are water-insoluble and when the vector agent for the application is water. Preferably, surfactant content may be comprised from 5% to 40% by weight of the composition.

Optionally, additional components may also be included, e.g. protective colloids, adhesives, thickeners, thixotropic agents, penetration agents, stabilisers, sequestering agents. More generally, the active compounds can be combined with any solid or liquid additive, which complies with the usual formulation techniques.

In general, the composition according to the invention may contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before application to the crop.

The compounds according to the invention can also be mixed with one or more insecticide, fungicide, bactericide, attractant, acaricide or pheromone active substance or other compounds with biological activity. The mixtures thus obtained have a broadened spectrum of activity.

The mixtures with other fungicide compounds are particularly advantageous. Examples of suitable fungicide mixing partners may be selected in the following lists:

B1) a compound capable to inhibit the nucleic acid synthesis like benalaxyl, benalaxyl-M, bupirimate, chiralaxyl, clozylacon, dimethirimol, ethirimol, furalaxyl, hymexazol, metalaxyl-M, ofurace, oxadixyl, oxolinic acid;

B2) a compound capable to inhibit the mitosis and cell division like benomyl, carbendazim, diethofencarb, fuberidazole, pencycuron, thiabendazole thiophanate-methyl, zoxamide;

B3) a compound capable to inhibit the respiration for example as CI-respiration inhibitor like diflumetorim;

as CII-respiration inhibitor like boscalid, carboxin, fenfuram, flutolanil, furametpyr, mepronil, oxycarboxine, penthiopyrad, thifluzamide;

as CIII-respiration inhibitor like azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin;

B4) a compound capable of to act as an uncoupler like dinocap, fluazinam;

B5) a compound capable to inhibit ATP production like fentin acetate, fentin chloride, fentin hydroxide, silthiofam;

B6) a compound capable to inhibit AA and protein biosynthesis like andoprim, blasticidin-S, cyprodinil, kasugamycin, kasugamycin hydrochloride hydrate, mepanipyrim, pyrimethanil;

B7) a compound capable to inhibit the signal transduction like fenpiclonil, fludioxonil, quinoxyfen;

B8) a compound capable to inhibit lipid and membrane synthesis like chlozolinate, iprodione, procymidone, vinclozolin, pyrazophos, edifenphos, iprobenfos (IBP), isoprothiolane, tolclofos-methyl, biphenyl, iodocarb, propamocarb, propamocarb-hydrochloride;

B9) a compound capable to inhibit ergosterol biosynthesis like fenhexamid, azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazol, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine;

B10) a compound capable to inhibit cell wall synthesis like benthiavalicarb, bialaphos, dimethomorph, flumorph, iprovalicarb, polyoxins, polyoxorim, validamycin A;

B11) a compound capable to inhibit melanine biosynthesis like carpropamid, diclocymet, fenoxanil, phtalide, pyroquilon, tricyclazole;

B12) a compound capable to induce a host defense like acibenzolar-5-methyl, probenazole, tiadinil;

B13) a compound capable to have a multisite action like captafol, captan, chlorothalonil, copper preparations such as copper hydroxide, copper naphthenate, copper oxychloride, copper sulphate, copper oxide, oxine-copper and Bordeaux mixture, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, propineb, sulphur and sulphur preparations including calcium polysulphide, thiram, tolylfluanid, zineb, ziram;

B14) a compound selected in the following list: amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulphate, diphenylamine, ethaboxam, ferimzone, flumetover, flusulfamide, fosetyl-aluminium, fosetyl-calcium, fosetyl-sodium, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, phosphorous acid and its salts, piperalin, propanosine-sodium, proquinazid, pyrrolnitrine, quintozene, tecloftalam, tecnazene, triazoxide, trichlamide, zarilamid and 2,3,5,6-tetrachloro-4-(methylsulfonyl)-pyridine, N-(4-Chloro-2-nitrophenyl)-N-ethyl-4-methyl-benzenesulfonamide, 2-amino-4-methyl-N-phenyl-5-thiazolecarboxamide, 2-chloro-N-(2,3-dihydro-1,1,3-trimethyl-1H-inden-4-yl)-3-pyridincarboxamide, 3-[5-(4-chlorophenyl)-2,3-dimethylisoxazolidin-3-yl]pyridine, cis-1-(4-chlorophenyl)-2-(1H-1,2,4-triazole-1-yl)-cycloheptanol, methyl 1-(2,3-dihydro-2,2-dimethyl-1H-inden-1-yl)-1H-imidazole-5-carboxylate, 3,4,5-trichloro-2,6-pyridinedicarbonitrile, Methyl 2-[[[cyclopropyl[(4-methoxyphenyl)imino]methyl]thio]methyl]-.alpha.-(methoxymethylene)-benzeneacetate, 4-Chloro-alpha-propynyloxy-N-[2-[3-methoxy-4-(2-propynyloxy)phenyl]ethyl]-benzeneacetamide, (2S)—N-[2-[4-[[3-(4-chlorophenyl)-2-propynyl]oxy]-3-methoxyphenyl]ethyl]-3-methyl-2-[(methylsulfonyl)amino]-butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propyl-benzopyranon-4-one, N-{(Z)-[(cyclopropylmethoxy)imino][6-(difluoromethoxy)-2,3-difluorophenyl]methyl}-2-phenylacetamide, N-(3-ethyl-3,5,5-trimethyl-cyclohexyl)-3-formylamino-2-hydroxy-benzamide, 2-[[[[1-[3(1 Fluoro-2-phenylethyl)oxy]phenyl]ethylidene]amino]oxy]methyl]-alpha-(methoxyimino)-N-methyl-alphaE-benzeneacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, 2-(2-{[6-(3-chloro-2-methylphenoxy)-5-fluoropyrimidin-4-yl]oxy}phenyl)-2-(methoxyimino)-N-methylacetamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid.

The composition according to the invention comprising a mixture of a compound of formula (I) with a bactericide compound may also be particularly advantageous. Examples of suitable bactericide mixing partners may be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The compound of formula (I) and the fungicide composition according to the invention can be used to curatively or preventively control the phytopathogenic fungi of plants or crops. Thus, according to a further aspect of the invention, there is provided a method for curatively or preventively controlling the phytopathogenic fungi of plants or crops characterised in that a compound of formula (I) or a fungicide composition according to the invention is applied to the seed, the plant or to the fruit of the plant or to the soil in which the plant is growing or in which it is desired to grow.

The method of treatment according to the invention may also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the overground parts of the plant such as trunks, stems or stalks, leaves, flowers and fruit of the concerned plant. Among the plants that can be protected by the method according to the invention, mention may be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons, oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots); horticultural and forest crops; as well as genetically modified homologues of these crops.

Among the diseases plants or crops that can be controlled by the method according to the invention, mention may be made of:

Powdery mildew diseases such as
  *Blumeria* diseases, caused for example by *Blumeria graminis;*
  *Podosphaera* diseases, caused for example by *Podosphaera leucotricha;*
  *Sphaerotheca* diseases, caused for example by *Sphaerotheca fuliginea;*
  *Uncinula* diseases, caused for example by *Uncinula necator,*
Rust diseases such as
  *Gymnosporangium* diseases, caused for example by *Gymnosporangium sabinae;*
  *Hemileia* diseases, caused for example by *Hemileia vastatrix,*

Phakopsora diseases, caused for example by *Phakopsora pachyrhizi* or *Phakopsora meibomiae*;
Puccinia diseases, caused for example by *Puccinia recondita*;
Uromyces diseases, caused for example by *Uromyces appendiculatus*;

Oomycete diseases such as:
Bremia diseases, caused for example by *Bremia lactucae*;
Peronospora diseases, caused for example by *Peronospora pisi* or *P. brassicae*;
Phytophthora diseases, caused for example by *Phytophthora infestans*;
Plasmopara diseases, caused for example by *Plasmopara viticola*;
Pseudoperonospora diseases, caused for example by *Pseudoperonospora humuli* or *Pseudoperonospora cubensis*;
Pythium diseases, caused for example by *Pythium ultimum*;

Leafspot, leaf blotch and leaf blight diseases such as
Alternaria diseases, caused for example by *Alternaria solani*;
Cercospora diseases, caused for example by *Cercospora beticola*;
Cladiosporum diseases, caused for example by *Cladiosporium cucumerinum*;
Cochliobolus diseases, caused for example by *Cochliobolus sativus*;
Colletotrichum diseases, caused for example by *Colletotrichum lindemuthanium*;
Cycloconium diseases, caused for example by *Cycloconium oleaginum*;
Diaporthe diseases, caused for example by *Diaporthe citri*;
Elsinoe diseases, caused for example by *Elsinoe fawcettii*;
Gloeosporium diseases, caused for example by *Gloeosporium laeticolor*;
Glomerella diseases, caused for example by *Glomerella cingulata*;
Guignardia diseases, caused for example by *Guignardia bidwelli*;
Leptosphaeria diseases, caused for example by *Leptosphaeria maculans*; *Leptosphaeria nodorum*;
Magnaporthe diseases, caused for example by *Magnaporthe grisea*;
Mycosphaerella diseases, caused for example by *Mycosphaerella graminicola*; *Mycosphaerella arachidicola*; *Mycosphaerella fijiensis*;
Phaeosphaeria diseases, caused for example by *Phaeosphaeria nodorurm*;
Pyrenophora diseases, caused for example by *Pyrenophora teres*;
Ramularia diseases, caused for example by *Ramularia collo-cygni*;
Rhynchosporium diseases, caused for example by *Rhynchosporium secalis*;
Septoria diseases, caused for example by *Septoria apii* or *Septoria lycopercisi*;
Typhula diseases, caused for example by *Typhula incarnata*;
Venturia diseases, caused for example by *Venturia inaequalis*;

Root and stem diseases such as:
Corticium diseases, caused for example by *Corticium graminearum*;
Fusarium diseases, caused for example by *Fusarium oxysporum*;
Gaeumannomyces diseases, caused for example by *Gaeumannomyces graminis*;
Rhizoctonia diseases, caused for example by *Rhizoctonia solani*;
Tapesia diseases, caused for example by *Tapesia acuformis*;
Thielaviopsis diseases, caused for example by *Thielaviopsis basicola*;

Ear and panicle diseases such as:
Alternaria diseases, caused for example by *Alternaria* spp.;
Aspergillus diseases, caused for example by *Aspergillus flavus*;
Cladosporium diseases, caused for example by *Cladosporium* spp.;
Claviceps diseases, caused for example by *Claviceps purpurea*;
Fusarium diseases, caused for example by *Fusarium culmorum*;
Gibberella diseases, caused for example by *Gibberella zeae*;
Monographella diseases, caused for example by *Monographella nivalis*;

Smut and bunt diseases such as:
Sphacelotheca diseases, caused for example by *Sphacelotheca reiliana*;
Tilletia diseases, caused for example by *Tilletia caries*;
Urocystis diseases, caused for example by *Urocystis occulta*;
Ustilago diseases, caused for example by *Ustilago nuda*;

Fruit rot and mould diseases such as:
Aspergillus diseases, caused for example by *Aspergillus flavus*;
Botrytis diseases, caused for example by *Botrytis cinerea*;
Penicillium diseases, caused for example by *Penicillium expansum*;
Sclerotinia diseases, caused for example by *Sclerotinia sclerotiorum*,
Verticilium diseases, caused for example by *Verticilium alboatrum*;

Seed and soilborne decay, mould, wilt, rot and damping-off diseases:
Fusarium diseases, caused for example by *Fusarium culmorum*;
Phytophthora diseases, caused for example by *Phytophthora cactorum*;
Pythium diseases, caused for example by *Pythium ultimum*;
Rhizoctonia diseases, caused for example by *Rhizoctonia solani*;
Sclerotium diseases, caused for example by *Sclerotium rolfsii*;
Microdochium diseases, caused for example by *Microdochium nivale*;

Canker, broom and dieback diseases such as
Nectria diseases, caused for example by *Nectria galligena*;

Blight diseases such as:
Monilinia diseases, caused for example by *Monilinia laxa*;

Leaf blister or leaf curl diseases such as:
Taphrina diseases, caused for example by *Taphrina deformans*;

Decline diseases of wooden plants such as:
Esca diseases, caused for example by *Phaemoniella clamydospora*;

Diseases of flowers and Seeds such as
Botrytis diseases, caused for example by *Botrytis cinerea*;

Diseases of tubers such as
Rhizoctonia diseases, caused for example by *Rhizoctonia solani*.

The fungicide composition according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention, or a composition according to the invention; this includes for example direct application, spraying, dipping, injection or any other suitable means.

The dose of active compound usually applied in the method of treatment according to the invention is generally and advantageously from 10 to 800 g/ha, preferably from 50 to 300 g/ha for applications in foliar treatment. The dose of active substance applied is generally and advantageously from 2 to 200 g per 100 kg of seed, preferably from 3 to 150 g per 100 kg of seed in the case of seed treatment.

It is clearly understood that the doses indicated herein are given as illustrative examples of the method according to the invention. A person skilled in the art will know how to adapt the application doses, notably according to the nature of the plant or crop to be treated.

The fungicide composition according to the invention may also be used in the treatment of genetically modified organisms with the compounds according to the invention or the agrochemical compositions according to the invention. Genetically modified plants are plants into genome of which a heterologous gene encoding a protein of interest has been stably integrated. The expression "heterologous gene encoding a protein of interest" essentially means genes which give the transformed plant new agronomic properties, or genes for improving the agronomic quality of the modified plant.

The compositions according to the invention may also be used for the preparation of composition useful to curatively or preventively treat human or animal fungal diseases such as, for example, mycoses, dermatoses, *trichophyton* diseases and candidiases or diseases caused by *Aspergillus* spp., for example *Aspergillus fumigatus*.

The various aspects of the invention will now be illustrated with reference to the following tables of compounds and examples. The following tables illustrate in a non-limiting manner examples of compounds according to the invention.

In the following examples, M+1 (or M−1) means the molecular ion peak, plus or minus 1 a.m.u. (atomic mass unit) respectively, as observed in mass spectroscopy and M (Apcl+) means the molecular ion peak as it was found via positive atmospheric pressure chemical ionisation in mass spectroscopy.

In the following examples, the logP values were determined in accordance with EEC Directive 79/831 Annex V.A8 by HPLC (High Performance Liquid Chromatography) on a reversed-phase column (C 18), using the method described below:

Temperature: 40° C.; Mobile phases: 0.1% aqueous formic acid and acetonitrile; linear gradient from 10% acetonitrile to 90% acetonitrile.

Calibration was carried out using unbranched alkan-2-ones (comprising 3 to 16 carbon atoms) with known logP values (determination of the logP values by the retention times using linear interpolation between two successive alkanones).

The lambda max values were determined in the maxima of the chromatographic signals using the UV spectra from 190 nm to 400 nm.

TABLE 1

| N° | A | $Z_1$ | $Z_2$ | X | Y | M+1 | LogP |
|---|---|---|---|---|---|---|---|
| 1 | furan-2-yl | H | H | 3-Cl | 5-CF3 | | 3.2 |
| 2 | furan-2-yl | Me | H | 3-Cl | 5-CF3 | | 3.6 |
| 3 | 3-methylfuran-2-yl | H | H | 3-Cl | 5-CF3 | | 3.78 |
| 4 | 3-methylfuran-2-yl | Me | H | 3-Cl | 5-CF3 | | 4.22 |

TABLE 1-continued

| N° | A | Z1 | Z2 | X | Y | M + 1 | LogP |
|---|---|---|---|---|---|---|---|
| 5 | 2,5-dimethylfuran-3-yl | H | H | 3-Cl | 5-CF3 | 373 | |
| 6 | 2-(trifluoromethyl)-5-methylfuran-3-yl | H | H | 3-Cl | 5-CF3 | | 4.26 |
| 7 | 2-(trifluoromethyl)-5-methylfuran-3-yl | Me | H | 3-Cl | 5-CF3 | | 5.19 |
| 8 | 2-methylfuran-3-yl | H | H | 3-Cl | 5-CF3 | | 3 |
| 9 | 4-(trifluoromethyl)-2-methyl-2H-1,2,3-triazol-5-yl | H | H | 3-Cl | 5-CF3 | | |
| 10 | 3-iodothiophen-2-yl | H | H | 3-Cl | 5-CF3 | 487 | |
| 11 | 3-iodothiophen-2-yl | H | H | H | 5-CF3 | | |
| 12 | 3-iodothiophen-2-yl | Me | H | 3-Cl | 5-CF3 | | 5.09 |

TABLE 1-continued

| N° | A | Z1 | Z2 | X | Y | M + 1 | LogP |
|---|---|---|---|---|---|---|---|
| 13 | 3-iodo-thiophen-2-yl | CF₃ | H | 3-Cl | 5-CF3 | | |
| 14 | 4-methoxy-thiophen-3-yl | H | H | 3-Cl | 5-CF3 | 391 | |
| 15 | 2-iodo-thiophen-3-yl | H | H | 3-Cl | 5-CF3 | | 4.17 |
| 16 | 2-iodo-thiophen-3-yl | Me | H | 3-Cl | 5-CF3 | | 4.95 |
| 17 | 4-trifluoromethyl-1-methyl-pyrrol-3-yl | H | H | 3-Cl | 5-CF3 | | 3.55 |
| 18 | 2-ethoxycarbonyl-3,5-dimethyl-1H-pyrrol-4-yl | H | H | 3-Cl | 5-CF3 | 444 | |
| 19 | 1-methyl-pyrrol-2-yl | H | H | 3-Cl | 5-CF3 | | |
| 20 | 4-methyl-oxazol-5-yl | H | H | 3-Cl | 5-CF3 | | 2.85 |

TABLE 1-continued

| N° | A | Z1 | Z2 | X | Y | M + 1 | LogP |
|---|---|---|---|---|---|---|---|
| 21 | 4,5-dimethyl-oxazol-5-yl (4-Me, connected at 5) | Me | H | 3-Cl | 5-CF3 | | 3.22 |
| 22 | 2,5-dimethyl-oxazol-4-yl | H | H | 3-Cl | 5-CF3 | | 3.11 |
| 23 | 2,5-dimethyl-oxazol-4-yl | Me | H | 3-Cl | 5-CF3 | | 3.46 |
| 24 | 2-methyl-5-trifluoromethyl-oxazol-4-yl | H | H | 3-Cl | 5-CF3 | | |
| 25 | 2-methyl-4-trifluoromethyl-thiazol-5-yl | H | H | 3-Cl | 5-CF3 | | 3.86 |
| 26 | 2-methyl-4-difluoromethyl-thiazol-5-yl | H | H | 3-Cl | 5-CF3 | | 3.41 |
| 27 | 2-methyl-4-difluoromethyl-thiazol-5-yl | Me | H | 3-Cl | 5-CF3 | | 4.34 |

TABLE 1-continued
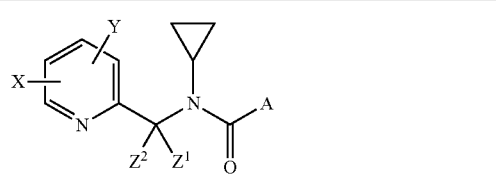
| N° | A | Z1 | Z2 | X | Y | M + 1 | LogP |
|---|---|---|---|---|---|---|---|
| 28 | 4-methyl-2-chloro-thiazol-5-yl | H | H | 3-Cl | 5-CF3 | 410 | |
| 29 | 2-methyl-thiazol-5-yl | H | H | 3-Cl | 5-CF3 | | 3.15 |
| 30 | 4-trifluoromethyl-2-methyl-thiazol-5-yl | Me | H | 3-Cl | 5-CF3 | | 4.80 |
| 31 | 2,5-dichloro-thiazol-4-yl | H | H | 3-Cl | 5-CF3 | | |
| 32 | 1,5-dimethyl-pyrazol-3-yl | H | H | 3-Cl | 5-CF3 | 373 | |
| 33 | 1,5-dimethyl-pyrazol-3-yl | Me | H | 3-Cl | 5-CF3 | | 3.15 |
| 34 | 3-difluoromethyl-1-methyl-pyrazol-4-yl | H | H | 3-Cl | 5-CF3 | 409 | |

TABLE 1-continued

| N° | A | Z1 | Z2 | X | Y | M + 1 | LogP |
|---|---|---|---|---|---|---|---|
| 35 | 1-methyl-3-(difluoromethyl)-1H-pyrazol-4-yl | Me | H | 3-Cl | 5-CF3 | | 3.78 |
| 36 | 1-methyl-3-(difluoromethyl)-1H-pyrazol-4-yl | CF3 | H | 3-Cl | 5-CF3 | | |
| 37 | 1-methyl-3-(difluoromethyl)-1H-pyrazol-4-yl | H | H | 6-Cl | 4-CF3 | | 3.1 |
| 38 | 1-methyl-3-(1-fluoroethyl)-1H-pyrazol-4-yl | H | H | 3-Cl | 5-CF3 | 405 | |
| 39 | 3-methoxy-1-methyl-1H-pyrazol-4-yl | H | H | 3-Cl | 5-CF3 | | 2.43 |
| 40 | 3-methoxy-1-methyl-1H-pyrazol-4-yl | Me | H | 3-Cl | 5-CF3 | | |
| 41 | 1-methyl-3-(trifluoromethyl)-1H-pyrazol-4-yl | H | H | 3-Cl | 5-CF3 | | 3.26 |

TABLE 1-continued
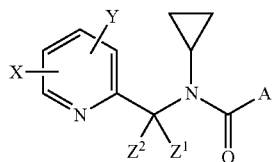
| N° | A | Z1 | Z2 | X | Y | M + 1 | LogP |
|---|---|---|---|---|---|---|---|
| 42 | (3-CF3-1-methylpyrazol-4-yl) | Me | H | 3-Cl | 5-CF3 | | 4.01 |
| 43 | (3-I-1-methylpyrazol-4-yl) | H | H | 3-Cl | 5-CF3 | | 2.82 |
| 44 | (3-OMe-5-Cl-1-methylpyrazol-4-yl) | H | H | 3-Cl | 5-CF3 | 423 | |
| 45 | (3-Me-5-F-1-methylpyrazol-4-yl) | H | H | 3-Cl | 5-CF3 | 391 | |
| 46 | (3-Me-5-F-1-methylpyrazol-4-yl) | Me | H | 3-Cl | 5-CF3 | | 3.67 |
| 47 | (3-Me-5-F-1-methylpyrazol-4-yl) | Et | H | 6-Cl | 4-CF3 | | 2.95 |
| 48 | (3-Me-5-F-1-methylpyrazol-4-yl) | CO2Me | H | 3-Cl | 5-CF3 | | 2.83 |
| 49 | (3-Me-5-F-1-methylpyrazol-4-yl) | H | H | H | 5-CF3 | | |

TABLE 1-continued
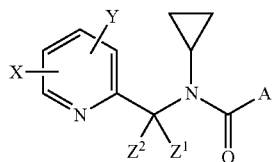
| N° | A | Z1 | Z2 | X | Y | M + 1 | LogP |
|---|---|---|---|---|---|---|---|
| 50 | (3-CF3, 5-F, 1-Me pyrazol-4-yl) | H | H | 3-Cl | 5-CF3 | 445 | |
| 51 | (3-CF3, 5-F, 1-Me pyrazol-4-yl) | Me | H | 3-Cl | 5-CF3 | | |
| 52 | (3-CF3, 5-F, 1-Me pyrazol-4-yl) | Et | H | 3-Cl | 5-CF3 | | |
| 53 | (3-CF3, 5-F, 1-Me pyrazol-4-yl) | CF3 | H | 3-Cl | 5-CF3 | | |
| 54 | (3-CHF2, 5-F, 1-Me pyrazol-4-yl) | H | H | 3-Cl | 5-CF3 | | |
| 55 | (3-Me, 1-Me pyrazol-4-yl) | H | H | 3-Cl | 5-CF3 | | 2.53 |
| 56 | (3-Me, 1-Me pyrazol-4-yl) | Me | H | 3-Cl | 5-CF3 | | 2.79 |

TABLE 1-continued

| N° | A | Z1 | Z2 | X | Y | M + 1 | LogP |
|---|---|---|---|---|---|---|---|
| 57 | 4-(5-chloro-1-methyl-1H-pyrazol-4-yl) | H | H | 3-Cl | 5-CF3 | | 3.92 |
| 58 | 4-(1-ethyl-5-fluoro-3-methyl-1H-pyrazol-4-yl) | H | H | 3-Cl | 5-CF3 | | 3.15 |
| 59 | 4-(3-ethyl-5-fluoro-1-methyl-1H-pyrazol-4-yl) | H | H | 3-Cl | 5-CF3 | | 3.11 |
| 60 | 4-(3-ethoxy-1-methyl-1H-pyrazol-4-yl)carbonyl | H | H | 3-Cl | 5-CF3 | | 2.75 |
| 61 | 5-(1-ethyl-4-methyl-1H-pyrazol-5-yl) | H | H | 3-Cl | 5-CF3 | 499 | |
| 62 | 5-(1,4-dimethyl-1H-pyrazol-5-yl) | H | H | 3-Cl | 5-CF3 | 373 | |
| 63 | 5-(1-phenyl-1H-pyrazol-5-yl) | H | H | 3-Cl | 5-CF3 | | 3.55 |
| 64 | 3-(5-methylisoxazol-3-yl) | H | H | 3-Cl | 5-CF3 | | 3.32 |

TABLE 1-continued

| N° | A | Z1 | Z2 | X | Y | M + 1 | LogP |
|---|---|---|---|---|---|---|---|
| 65 | 5-methylisoxazol-3-yl | Me | H | 3-Cl | 5-CF3 | | 3.63 |
| 66 | 5-methylisoxazol-4-yl | H | H | 3-Cl | 5-CF3 | | |
| 67 | 3-methylisoxazol-4-yl | H | H | 3-Cl | 5-CF3 | 360 | |
| 68 | 3,5-dimethylisoxazol-4-yl | H | H | 3-Cl | 5-CF3 | | 3 |
| 69 | 3-(4-chlorophenyl)-5-methylisoxazol-4-yl | H | H | 3-Cl | 5-CF3 | | 4.48 |
| 70 | 3-bromoisoxazol-5-yl | H | H | 3-Cl | 5-CF3 | | |
| 71 | isoxazol-5-yl | H | H | 3-Cl | 5-CF3 | | 3.72 |
| 72 | 3-methyl-5-trifluoromethylisoxazol-4-yl | H | H | 3-Cl | 5-CF3 | | |
| 73 | 3-methylthio-5-methylisothiazol-4-yl | H | H | 3-Cl | 5-CF3 | | |

TABLE 1-continued
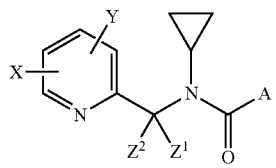
| N° | A | Z1 | Z2 | X | Y | M + 1 | LogP |
|---|---|---|---|---|---|---|---|
| 74 |  | H | H | 3-Cl | 5-CF3 | 430 | |
TABLE 2
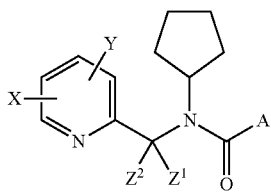
| N° | A | Z1 | Z2 | X | Y | M + 1 | LogP |
|---|---|---|---|---|---|---|---|
| 75 |  | H | H | 3-Cl | 5-CF3 | 389 | |
| 76 | | H | H | 3-Cl | 5-CF3 | | |
| 77 |  | H | H | 3-Cl | 5-CF3 | 419 | |
| 78 |  | H | H | 3-Cl | 5-CF3 | | |
TABLE 2-continued
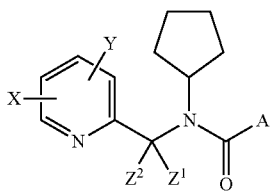
| N° | A | Z1 | Z2 | X | Y | M + 1 | LogP |
|---|---|---|---|---|---|---|---|
| 79 | | H | H | 3-Cl | 5-CF3 | | 3.68 |
| 80 | | H | H | 3-Cl | 5-CF3 | | 3.32 |
| 81 | | H | H | 3-Cl | 5-CF3 | | 4.25 |
| 82 | | H | H | 3-Cl | 5-CF3 | | 4.15 |

TABLE 3
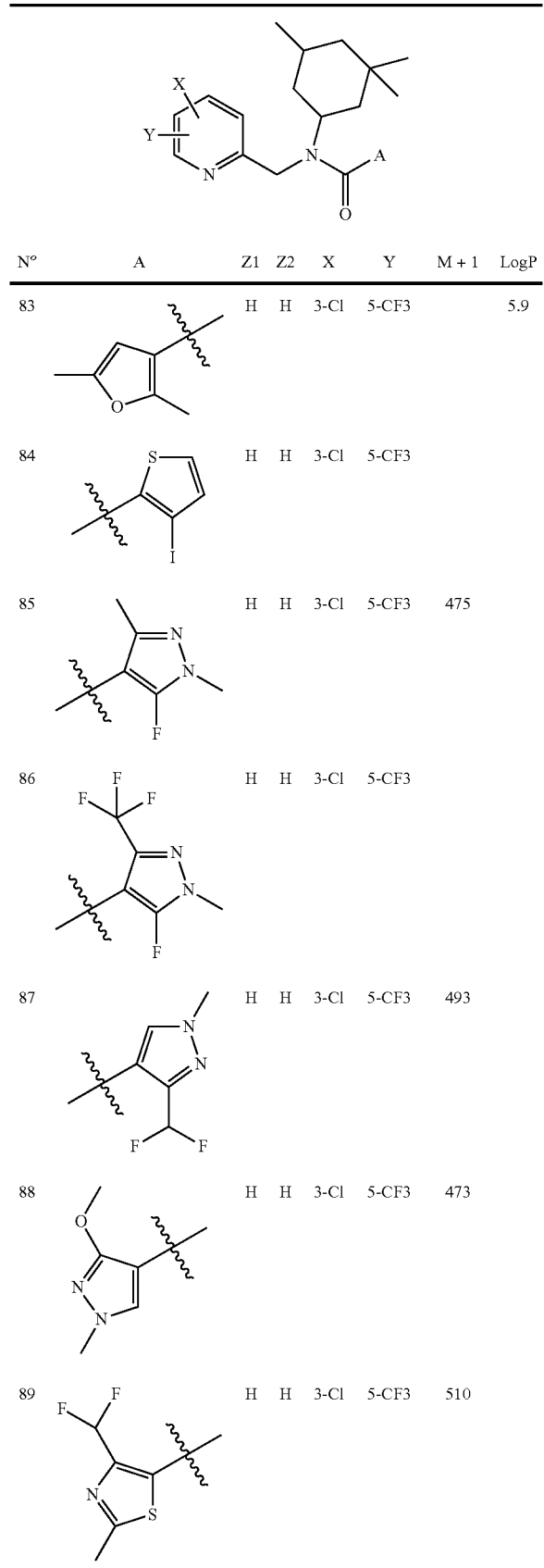
TABLE 3-continued
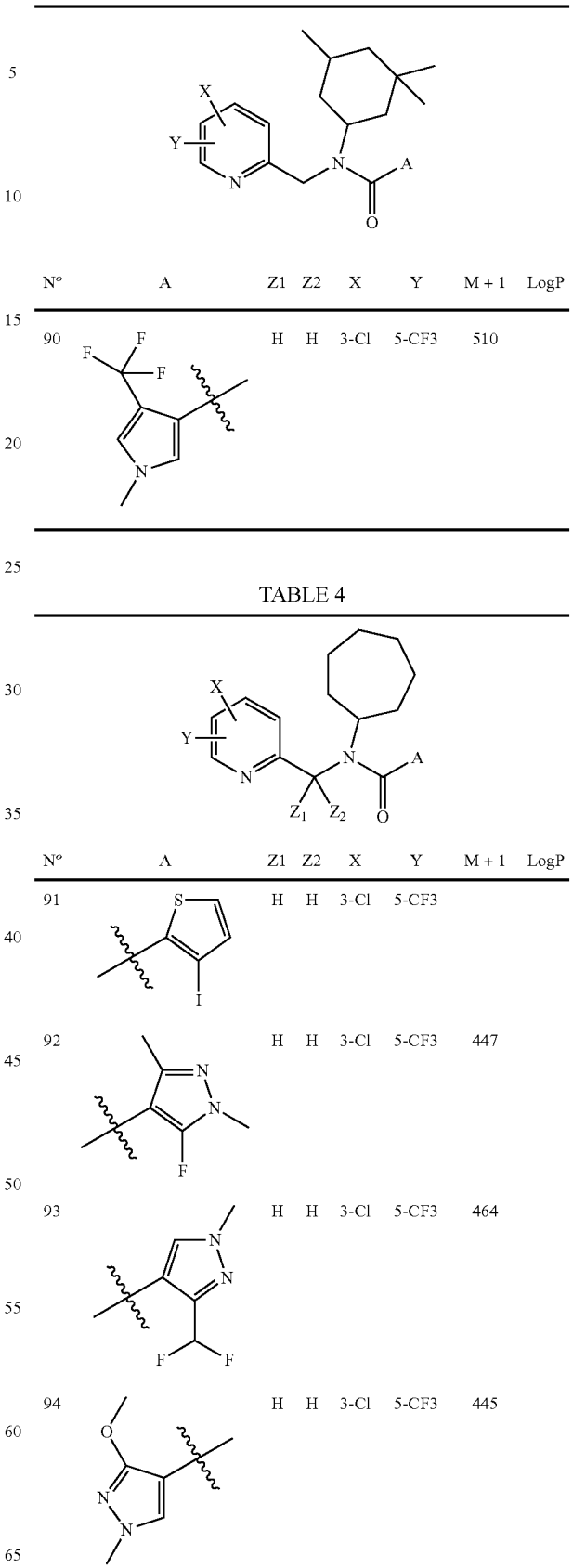

TABLE 4-continued

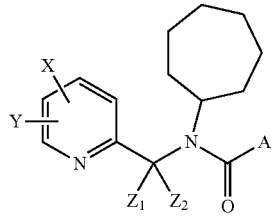

| N° | A | Z1 | Z2 | X | Y | M + 1 | LogP |
|---|---|---|---|---|---|---|---|
| 95 | ![F-CH(F)-thiazole-methyl] | H | H | 3-Cl | 5-CF3 | | |
| 96 | ![CF3-pyrrole-N-methyl] | H | H | 3-Cl | 5-CF3 | 482 | |

The following examples illustrate in a non-limiting manner the preparation and efficacy of the compounds of formula (I) according to the invention.

PREPARATION EXAMPLE

N-{[3-chloro-5-(trifluoromethyl)pyridin-2-yl]methyl}-N-cyclopropyl-5-fluoro-1,3-dimethyl-1H-pyrazole-4-carboxamide (compound 45)

A solution of 2.7 g (10.7 mmol) of N-{[3-chloro-5-(trifluoromethyl)pyridin-2-yl]methyl}cyclopropylamine, 1.9 g (10.7 mmol) of 5-fluoro-1,3-dimethyl-1H-pyrazole-4-carbonyl chloride and 3.0 ml (21.5 mmol) of triethylamine in THF (60 ml) is stirred at room temperature for 1 hr.

Solvent is removed under reduced pressure. Residue is partitioned between aqueous hydrochloric acid and ethylacetate. Organic phase is separated, washed with aqueous potassium carbonate, dried over magnesium sulfate and solvent evaporated. The resulting viscous oil is dissolved in heptane and after 2 mins a white solid crashed out which is filtered off and dried to give 3.45 g of desired N-{[3-chloro-5-(trifluoromethyl)pyridin-2-yl]methyl}-N-cyclopropyl-5-fluoro-1,3-dimethyl-1H-pyrazole-4-carboxamide as a white solid.

Mass spectrum: [M+1]=391

EFFICACY EXAMPLE A

In vivo test on *Leptosphaeria* Test (Leaf Spot of Wheat)

Solvent: 49 parts by weight of N,N-dimethylformamide
Emulsifier: 1 part by weight of alkylaryl polyglycol ether
To produce a suitable preparation of active compound, 1 part by weight of active compound is mixed with the stated amounts of solvent and emulsifier, and the concentrate is diluted with water to the desired concentration.

Young plants are sprayed with a preparation of active compound at the stated rate of application. After the spray coating has dried on, the plants are sprayed with a spore suspension of *Leptosphaeria nodorum*. The plants remain for 48 hours in an incubation cabinet at 20° C. and a relative atmospheric humidity of 100%. The plants are placed in a greenhouse at a temperature of approximately 22° C. and a relative atmospheric humidity of approximately 100%.

The test is evaluated 12-14 days after inoculation. Under these conditions, good (at least 70% of disease control) to total protection (100% of disease control) is observed at a dose of 500 ppm with the following compounds: 45 and 50 according to the invention whereas weak protection (less than 30% of disease control) to no protection at all is observed at a dose of 500 ppm with the compounds of examples 2, 8 and 50 disclosed in patent application WO-01/11966. Examples 2, 8 and 50 disclosed in patent application WO-01/11966 correspond, respectively, to following compounds:

N-{[3-chloro-5-(trifluoromethyl)pyridin-2-yl]methyl}thiophene-2-carboxamide
N-{[3-chloro-5-(trifluoromethyl)pyridin-2-yl]methyl}-1-phenyl-5-(trifluoromethyl)-1H-pyrazole-4-carboxamide
2-bromo-N-{[3-chloro-5-(trifluoromethyl)pyridin-2-yl]methyl}-4-(trifluoromethyl)-1,3-thiazole-5-carboxamide.

These results show that the compounds according to the invention have a much better biological activity than the structurally closest compounds disclosed in WO01/11966.

EFFICACY EXAMPLE B

In Vivo Test on *Erysiphe gramini* (Powdery Mildew on Barley)

Solvent: 49 parts by weight of N,N-dimethylformamide
Emulsifier: 1 part by weight of alkylaryl polyglycol ether
To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are dusted with spores of *Erysiphe graminis* f.sp. *hordei*. The plants are placed in a greenhouse at a temperature of approximately 18° C. and a relative atmospheric humidity of approximately 70% to promote the development of mildew pustules.

The test is evaluated 7 days after inoculation. Under these conditions, good (at least 70% of disease control) to total protection (100% of disease control) is observed at a dose of 500 ppm with the following compounds: 45 and 50 according to the invention whereas weak protection (less than 30% of disease control) to no protection at all is observed at a dose of 500 ppm with the compounds of examples 2, 8 and 50 disclosed in patent application WO-01/11966. Again, this confirm that the compounds according to the invention have a much better biological activity than the structurally closest compounds disclosed in WO-01/11966.

EFFICACY EXAMPLE C

In Vivo Test on *Pyrenophora Teres* (Barley Net Blotch)

Solvent: 10% by volume of acetone
5% by volume of dimethylsulfoxide
85% by volume of water
Emulsifier: Tween 80: 0.5 μl per mg of a.i.

The active ingredient tested is mixed with the appropriate amount of solvent and emulsifier to obtain the desired active material concentration.

Barley plants (Express or Plaisant variety) in starter cups, sown on a 50/50 peat soil-Pozzolana substrate and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Pyrenophora teres* spores (12,000 spores per ml). The spores are collected from a 12-day-old culture. The contaminated barley plants are incubated for 24 hours at about 20° C. and at 100% relative humidity, and then for 12 days at 80% relative humidity.

Grading is carried out 12 days after the contamination, in comparison with the control plants. Under these conditions, good (at least 70%) to total protection is observed at a dose of 500 ppm with the following compounds: 5, 6, 7, 12, 15, 16, 27, 30, 35, 37, 42, 45, 46, 47, 50 and 55.

EFFICACY EXAMPLE D

In Vivo Test on *Puccinia recondita* f. Sp. *tritici* (wheat Brown Rust)

Solvent: 10% by volume of acetone
5% by volume of dimethylsulfoxide
85% by volume of water
Emulsifier: Tween 80: 0.5 µl per mg of a.i.

The active ingredient tested is mixed with the appropriate amount of solvent and emulsifier to obtain the desired active material concentration.

Wheat plants (Scipion variety) in starter cups, sown on a 50/50 peat soil-Pozzolana substrate and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Puccinia recondita* f. sp. *tritici* spores (100,000 spores per ml). The spores are collected from a 10-day-old culture on plants. The contaminated wheat plants are incubated for 48 hours at about 20° C. and at 100% relative humidity, and then for 10 days at 80% relative humidity.

Grading is carried out 10 days after the contamination, in comparison with the control plants. Under these conditions, good (at least 60%) to total protection is observed at a dose of 500 ppm with the following compound: 5, 26, 45 and 50.

EFFICACY EXAMPLE E

In Vivo Test on *Alternaria brassicae* (Leaf Spot of Crucifers)

Solvent: 10% by volume of acetone
5% by volume of dimethylsulfoxide
85% by volume of water
Emulsifier: Tween 80: 0.5 µl per mg of a.i.

The active ingredient tested is mixed with the appropriate amount of solvent and emulsifier to obtain the desired active material concentration.

Radish plants (Pernot variety) in starter cups, sown on a 50/50 peat soil-Pozzolana substrate and grown at 18-20° C., are treated at the cotyledon stage by spraying with the aqueous suspension described above.

Plants, used as controls, are treated with an aqueous solution not containing the active material. After 24 hours, the plants are contaminated by spraying them with an aqueous suspension of *Alternaria brassicae* spores (40,000 spores per $cm^3$). The spores are collected from a 12-13-day-old culture. The contaminated radish plants are incubated for 67 days at about 18° C., under a humid atmosphere.

Grading is carried out 6 to 7 days after the contamination, in comparison with the control plants. Under these conditions, good (at least 70%) to total protection is observed at a dose of 500 ppm with the following compound: 6, 7, 12, 16, 23, 27, 30, 35, 42, 46, 50 and 56.

The invention claimed is:
1. A compound of formula (I)

$$\text{(X)}_n \text{—} \underset{Z^2 \ Z^1 \ O}{\text{Ar}} \text{—} C(Z^1)(Z^2)\text{—}N(Z^3)\text{—}C(O)\text{—}A$$

wherein
A is a substituted or non substituted 5-membered heterocyclyl group linked to the carbonyl through a carbon atom;
$Z^1$ and $Z^2$ are independently selected from the group consisting of a hydrogen atom; $C_1$-$C_5$-alkyl; $C_2$-$C_5$-alkenyl; $C_1$-$C_5$-alkynyl; cyano; nitro; a halogen atom; $C_1$-$C_5$-alkoxy; $C_2$-$C_5$-alkenyloxy; $C_2$-$C_5$-alkynyloxy; $C_3$-$C_7$-cycloalkyl; $C_1$-$C_5$-alkylsulfenyl; an amino; $C_1$-$C_5$-alkylamino; di-$C_1$-$C_5$-alkylamino; $C_1$-$C_5$-alkoxycarbonyl; $C_1$-$C_5$-alkylcarbamoyl; di-$C_1$-$C_5$-alkylcarbamoyl; and N—$C_1$-$C_5$-alkyl-$C_1$-$C_5$-alkoxycarbamoyl; or
$Z^1$ and $Z^2$ together with the carbon atom to which they are bonded can form a 3-, 4-, 5- or 6-membered carbo- or heterocyclic ring, which can be substituted;
$Z^3$ is cyclopropyl;
Y is a $C_1$-$C_5$-halogenoalkyl comprising up to 5 halogen atoms which can be the same or different;
each X is independently selected from the group consisting of a halogen atom; nitro; cyano; hydroxyl; a carboxyl group; $C_1$-$C_8$-alkyl; $C_1$-$C_6$-halogenoalkyl comprising up to 5 halogen atoms which can be the same or different; $C_1$-$C_9$, alkylamino; di-$C_1$-$C_8$-alkylamino; $C_1$-$C_8$-alkoxy; $C_1$-$C_6$-halogenoalkoxy comprising up to 5 halogen atoms which can be the same or different; $C_1$-$C_8$-alkylthio; $C_1$-$C_6$-halogenoalkylthio comprising up to 5 halogen atoms which can be the same or different; $C_2$-$C_8$-alkenyloxy; $C_2$-$C_8$halogenoalkenyloxy comprising up to 5 halogen atoms which can be the same or different; $C_3$-$C_8$-alkynyloxy; $C_3$-$C_8$-halogenoalkynyloxy comprising up to 5 halogen atoms which can be the same or different; $C_3$-$C_8$-cycloalkyl; $C_1$-$C_8$-alkoxycarbonyl; $C_1$-$C_8$-alkylsulfinyl; $C_1$-$C_8$-alkylsulfonyl; $C_1$-$C_8$-halogenoalkylsulfinyl comprising up to 5 halogen atoms which can be the same or different;
$C_1$-$C_8$-halogenoalkylsulfonyl comprising up to 5 halogen atoms which can be the same or different, and or $C_1$-$C_6$-alkoximino-$C_1$-$C_6$-alkyl;
n=0, 1, 2 or 3;
as well as any salt or optically active isomer thereof.
2. The compound of claim 1 wherein A is selected from the group consisting of:

a heterocycle of formula (A¹)

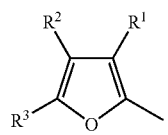
(A¹)

wherein:
$R^1$, $R^2$, and $R^3$ are independently selected from the group consisting of a hydrogen atom; a halogen at $C_1$-$C_5$-alkyl; and a $C_1$-$C_5$-halogenoalkyl comprising up to 5 halogen atoms which can be the same or different;

a heterocycle of formula (A²)

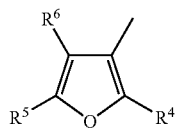
(A²)

wherein:
$R^4$, $R^5$, and $R^6$ are independently selected from the group consisting of a hydrogen atom; a halogen atom; $C_1$-$C_5$-alkyl; and $C_1$-$C_5$-halogenoalkyl comprising up to 5 halogen atoms which can be the same or different;

a heterocycle of formula (A³)

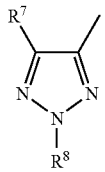
(A³)

wherein:
$R^7$ is selected from the group consisting of a hydrogen atom; a halogen atom; $C_1$-$C_5$-alkyl; and $C_1$-$C_5$-halogenoalkyl comprising up to 5 halogen atoms which can be the same or different; and
$R^8$ is selected from the group consisting of a hydrogen atom; $C_1$-$C_5$-alkyl; and a phenyl substituted by a halogen atom or by a $C_1$-$C_5$-alkyl;

a heterocycle of formula (A⁴)

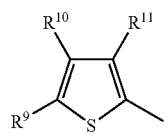
(A⁴)

wherein:
$R^9$, $R^{10}$, and $R^{11}$ are independently selected from the group consisting of a hydrogen atom; a halogen atom; $C_1$-$C_5$-alkyl; an amino; $C_1$-$C_5$-alkoxy; $C_1$-$C_5$-alkylthio; and $C_1$-$C_5$-halogenoalkyl comprising up to 5 halogen atoms which can be the same or different;

a heterocycle of formula (A⁵)

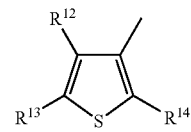
(A⁵)

wherein:
$R^{12}$ and $R^{13}$ are independently selected from the group consisting of a hydrogen atom; a halogen atom; $C_1$-$C_5$-alkyl; $C_1$-$C_5$-alkoxy; an amino; and $C_1$-$C_5$-halogenoalkyl comprising up to 5 halogen atoms which can be the same or different; and
$R^{14}$ is selected from the group consisting of a hydrogen atom; a halogen atom; $C_1$-$C_5$-alkyl; an amino; and $C_1$-$C_5$-halogenoalkyl comprising up to 5 halogen atoms which can be the same or different;

a heterocycle of formula (A⁶)

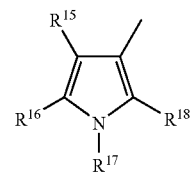
(A⁶)

wherein:
$R^{15}$ is selected from the group consisting of a hydrogen atom; a halogen atom; a, cyano; $C_1$-$C_5$-alkyl; and $C_1$-$C_5$-halogenoalkyl comprising up to 5 halogen atoms which can be the same or different;
$R^{16}$ and $R^{18}$ are independently selected from the group consisting of a hydrogen atom; a halogen atom; $C_1$-$C_5$-alkoxycarbonyl; $C_1$-$C_5$-alkyl; and $C_1$-$C_5$-halogenoalkyl comprising up to 5 halogen atoms which can be the same or different; and
$R^{17}$ is selected from the group consisting of a hydrogen atom; or $C_1$-$C_5$-alkyl; $C_1$-$C_5$-halogenoalkyl comprising up to 5 halogen atoms which can be the same or different; and a phenyl substituted by a halogen atom or by a $C_1$-$C_5$-alkyl;

a heterocycle of formula (A⁷)

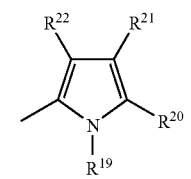
(A⁷)

wherein:
$R^{19}$ is selected from the group consisting of a hydrogen atom; $C_1$-$C_5$-alkyl; and a phenyl substituted by a halogen atom or by a $C_1$-$C_5$-alkyl; and
$R^{20}$, $R^{21}$, and $R^{22}$ are independently selected from the group consisting of a hydrogen atom; a halogen atom; $C_1$-$C_5$-alkyl; and $C_1$-$C_5$-halogenoalkyl comprising up to 5 halogen atoms which can be the same or different;

a heterocycle of formula (A⁸)

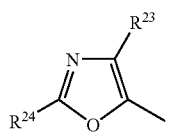
(A⁸)

wherein:
$R^{23}$ is selected from the group consisting of a hydrogen atom; a halogen atom; $C_1$-$C_5$-alkyl; and $C_1$-$C_5$-halogenoalkyl comprising up to 5 halogen atoms which can be the same or different; and
$R^{24}$ is selected from the group consisting of a hydrogen atom and $C_1$-$C_5$-alkyl; a heterocycle of formula (A⁹)

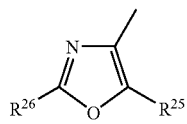
(A⁹)

wherein:
$R^{25}$ is selected from the group consisting of a halogen atom; $C_1$-$C_5$-alkyl; and $C_1$-$C_5$-halogenoalkyl comprising up to 5 halogen atoms which can be the same or different; and
$R^{26}$ is selected from the group consisting of a hydrogen atom and $C_1$-$C_5$-alkyl; a heterocycle of formula (A¹⁰)

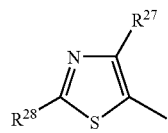
(A¹⁰)

wherein:
$R^{27}$ is selected from the group consisting of a halogen atom; $C_1$-$C_5$-alkyl; and $C_1$-$C_5$-halogenoalkyl comprising up to 5 halogen atom; which can be the same or different; and
$R^{28}$ is selected from the group consisting of a hydrogen atom; a halogen atom; an amino; $C_1$-$C_5$-alkyl; $C_1$-$C_5$-halogenoalkyl comprising up to 5 halogen atoms which can be the same or different; and a phenyl substituted by a halogen atom or by a $C_1$-$C_5$-alkyl;
a heterocycle of formula (A¹¹)

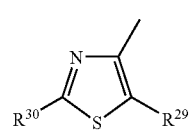
(A¹¹)

wherein:
$R^{29}$ is selected from the group consisting of a hydrogen atom; a halogen atom; $C_1$-$C_5$-alkyl; and $C_1$-$C_5$-halogenoalkyl comprising up to 5 halogen atoms which can be the same or different; and $R^{30}$ is selected from the group consisting of a hydrogen atom; a halogen atom; $C_1$-$C_5$-alkyl; $C_1$-$C_5$-halogenoalkyl comprising up to 5 halogen atoms which can be the same or different; an amino; $C_1$-$C_5$-alkylamino; and di-$C_1$-$C_5$-alkylamino;

a heterocycle of formula (A¹²)

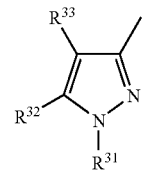
(A¹²)

wherein:
$R^{31}$ is selected from the group consisting of a hydrogen atom; a halogen atom; $C_1$-$C_5$-alkyl; and a phenyl substituted by a halogen atom or by a $C_1$-$C_5$-alkyl;
$R^{32}$ is selected from the group consisting of a hydrogen atom; a halogen atom; $C_1$-$C_5$-alkyl; and $C_1$-$C_5$-halogenoalkyl comprising up to 5 halogen atoms which can be the same or different; and
$R^{33}$ is selected from the group consisting of a hydrogen atom; a halogen atom; a nitro; and $C_1$-$C_5$-halogenoalkyl comprising up to 5 halogen atoms which can be the same or different;

a heterocycle of formula (A¹³)

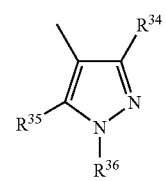
(A¹³)

wherein:
$R^{34}$ is selected from the group consisting of a hydrogen atom; a halogen atom; $C_1$-$C_5$-alkyl; $C_3$-$C_5$-cycloalkyl; $C_1$-$C_5$-halogenoalkyl comprising up to 5 halogen atoms which can be the same or different; $C_1$-$C_5$-alkoxy; $C_2$-$C_5$-alkynyloxy; $C_1$-$C_5$-halogenoalkoxy comprising up to 5 halogen atoms which can be the same or different; and a phenyl substituted by a halogen atom or by a $C_1$-$C_5$-alkyl;
$R^{35}$ is selected from the group consisting of a hydrogen atom; a halogen atom; $C_1$-$C_5$-alkyl; a cyano; $C_1$-$C_5$-alkoxy; $C_1$-$C_5$-alkylthio; $C_1$-$C_5$-halogenoalkyl comprising up to 5 halogen atoms which can be the same or different; $C_1$-$C_5$-halogenoalkoxy comprising up to 5 halogen atoms which can be the same or different; an amino; $C_1$-$C_5$-alkylamino; and di($C_1$-$C_5$-alkyl); and
$R^{36}$ is selected from the group consisting of a hydrogen atom; $C_1$-$C_5$-alkyl; and a phenyl substituted by a halogen atom or by a $C_1$-$C_5$-alkyl;

a heterocycle of formula ($A^{14}$)

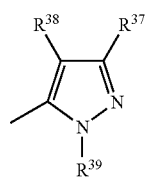

($A^{14}$)

wherein:
$R^{37}$ and $R^{38}$ are independently selected from the group consisting of a hydrogen atom; a halogen atom; $C_1$-$C_5$-alkyl; $C_1$-$C_5$-halogenoalkyl comprising up to 5 halogen atoms which can be the same or different; $C_1$-$C_5$-alkoxy; and a $C_1$-$C_5$-alkylthio; and
$R^{39}$ is selected from the group consisting of a hydrogen atom; $C_1$-$C_5$-alkyl; and a phenyl substituted by a halogen atom or by a $C_1$-$C_5$-alkyl;
a heterocycle of formula ($A^{15}$)

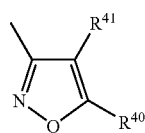

($A^{15}$)

wherein:
$R^{40}$ and $R^{41}$ are independently selected from the group consisting of a hydrogen atom; a halogen atom; $C_1$-$C_5$-alkyl; and $C_1$-$C_5$-halogenoalkyl comprising up to 5 halogen atoms which can be the same or different;
a heterocycle of formula ($A^{16}$)

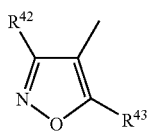

($A^{16}$)

wherein:
$R^{42}$ and $R^{43}$ are independently selected from the group consisting of a hydrogen atom; $C_1$-$C_5$-alkyl; $C_1$-$C_5$-halogenoalkyl comprising up to 5 halogen atoms which can be the same or different; an amino; and a phenyl substituted by a halogen atom or by a $C_1$-$C_5$-alkyl;
a heterocycle of formula ($A^{17}$)

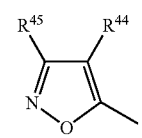

($A^{17}$)

wherein:
$R^{44}$ and $R^{45}$ are independently selected from the group consisting of a hydrogen atom; a halogen atom; $C_1$-$C_5$-alkyl; and $C_1$-$C_5$-halogenoalkyl comprising up to 5 halogen atoms which can be the same or different;

a heterocycle of formula ($A^{18}$)

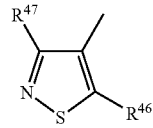

($A^{18}$)

wherein:
$R^{46}$ is selected from the group consisting of a hydrogen atom; $C_1$-$C_5$-alkyl; $C_1$-$C_5$-halogenoalkyl comprising up to 5 halogen atoms which can be the same or different; and $C_1$-$C_5$-alkylsulfanyl; and
$R^{47}$ is selected from the group consisting of a hydrogen atom; a halogen atom; and $C_1$-$C_5$-alkyl;
a heterocycle of formula ($A^{19}$)

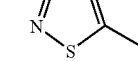

($A^{19}$)

wherein:
$R^{48}$ and $R^{49}$ are independently selected from the group consisting of a hydrogen atom; a halogen atom; $C_1$-$C_5$-alkyl; and $C_1$-$C_5$-halogenoalkyl comprising up to 5 halogen atoms which can be the same or different;
and
a heterocycle of formula ($A^{20}$)

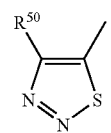

($A^{20}$)

wherein:
$R^{50}$ is selected from the group consisting of a halogen atom; $C_1$-$C_5$-alkyl; and $C_1$-$C_5$-halogenoalkyl comprising up to 5 halogen atoms which can be the same or different.

3. The compound of claim 2 wherein A is selected from the group consisting of:
a heterocycle of formula ($A^{13}$)

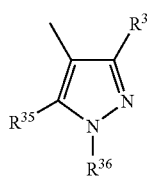

($A^{13}$)

wherein
$R^{34}$ is selected from the group consisting of a hydrogen atom; a halogen atom; $C_1$-$C_5$-alkyl; $C_3$-$C_5$-cycloalkyl; $C_1$-$C_5$-halogenoalkyl comprising up to 5 halogen atoms which can be the same or different; $C_1$-$C_5$-alkoxy;

$C_1$-$C_5$-alkynyloxy; $C_1$-$C_5$-halogenoalkoxy comprising up to 5 halogen atoms which can be the same or different; and a phenyl substituted by a halogen atom or by a $C_1$-$C_5$-alkyl;

$R^{35}$ is selected from the group consisting of a hydrogen atom; a halogen atom; $C_1$-$C_5$-alkyl; a cyano; $C_1$-$C_5$-alkoxy; $C_1$-$C_5$-alkylthio; $C_1$-$C_5$-halogenoalkyl comprising up to 5 halogen atoms which can be the same or different; $C_1$-$C_5$-halogenoalkoxy comprising up to 5 halogen atoms which can be the same or different; an amino; $C_1$-$C_5$-alkylamino; and di($C_1$-$C_5$-alkyl); and $R^{36}$ is selected from the group consisting of a hydrogen atom; $C_1$-$C_5$-alkyl; and a phenyl substituted by a halogen atom or by a $C_1$-$C_5$-alkyl;

and a 5-membered heterocycle that is substituted in position ortho.

4. The compound of claim 1 wherein each X is independently selected from the group consisting of a halogen atom; $C_1$-$C_8$-alkyl; $C_1$-$C_6$-halogenoalkyl comprising up to 5 halogen atoms which can be the same or different; $C_1$-$C_8$-alkoxy; and $C_1$-$C_6$-halogenoalkoxy comprising up to 5 halogen atoms which can be the same or different.

5. The compound of claim 1 wherein n=1.

6. The compound of claim 1 wherein Y is trifluoromethyl.

7. A compound of formula (I)

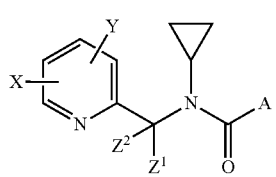

(I)

wherein

A is a substituted or non substituted 5-membered heterocyclyl group linked to the carbonyl through a carbon atom and selected from the group consisting of:

a heterocycle of formula ($A^1$)

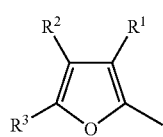

($A^1$)

wherein:

$R^1$, $R^2$, and $R^3$ are independently selected from the group consisting of a hydrogen atom; a halogen at $C_1$-$C_5$-alkyl; and a $C_1$-$C_5$-halogenoalkyl comprising up to 5 halogen atoms which can be the same or different;

a heterocycle of formula ($A^2$)

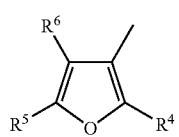

($A^2$)

wherein:

$R^4$, $R^5$, and $R^6$ are independently selected from the group consisting of a hydrogen atom; a halogen atom; $C_1$-$C_5$-alkyl; and $C_1$-$C_5$-halogenoalkyl comprising up to 5 halogen atoms which can be the same or different;

a heterocycle of formula ($A^3$)

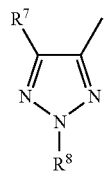

($A^3$)

wherein:

$R^7$ is selected from the group consisting of a hydrogen atom; a halogen atom; $C_1$-$C_5$-alkyl; and $C_1$-$C_5$-halogenoalkyl comprising up to 5 halogen atoms which can be the same or different; and $R^8$ is selected from the group consisting of a hydrogen atom; $C_1$-$C_5$-alkyl; and a phenyl substituted by a halogen atom or by a $C_1$-$C_5$-alkyl;

a heterocycle of formula ($A^4$)

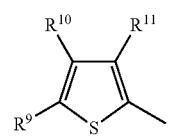

($A^4$)

wherein:

$R^9$, and $R^{10}$, and $R^{11}$ are independently selected from the group consisting of a hydrogen atom; a halogen atom; $C_1$-$C_5$-alkyl; an amino; $C_1$-$C_5$-alkoxy; $C_1$-$C_5$-alkylthio; and $C_1$-$C_5$-halogenoalkyl comprising up to 5 halogen atoms which can be the same or different;

a heterocycle of formula ($A^5$)

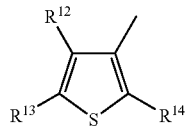

($A^5$)

wherein:

$R^{12}$ and $R^{13}$ are independently selected from the group consisting of a hydrogen atom; a halogen atom; $C_1$-$C_5$-alkyl; $C_1$-$C_5$-alkoxy; an amino; and $C_1$-$C_5$-halogenoalkyl comprising up to 5 halogen atoms which can be the same or different; and $R^{14}$ is selected from the group consisting of a hydrogen atom; a halogen atom; $C_1$-$C_5$-alkyl; an amino; and $C_1$-$C_5$-halogenoalkyl comprising up to 5 halogen atoms which can be the same or different;

a heterocycle of formula (A⁶)

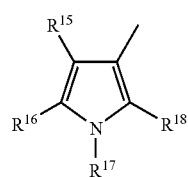

wherein:
- $R^{15}$ is selected from the group consisting of a hydrogen atom; a halogen atom; a cyano; $C_1$-$C_5$-alkyl; and $C_1$-$C_5$-halogenoalkyl comprising up to 5 halogen atoms which can be the same or different;
- $R^{16}$ and $R^{18}$ are independently selected from the group consisting of a hydrogen atom; a halogen atom; $C_1$-$C_5$-alkoxycarbonyl; $C_1$-$C_5$-alkyl; and $C_1$-$C_5$-halogenoalkyl comprising up to 5 halogen atoms which can be the same or different; and
- $R^{17}$ is selected from the group consisting of a hydrogen atom; $C_1$-$C_5$-alkyl; $C_1$-$C_5$-halogenoalkyl comprising up to 5 halogen atoms which can be the same or different; and a phenyl substituted by a halogen atom or by a $C_1$-$C_5$-alkyl;

a heterocycle of formula (A⁷)

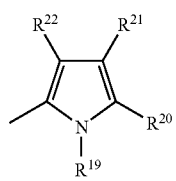

wherein:
- $R^{19}$ is selected from the group consisting of a hydrogen atom; $C_1$-$C_5$-alkyl; and a phenyl substituted by a halogen atom or by a $C_1$-$C_5$-alkyl; and
- $R^{20}$, $R^{21}$, and $R^{22}$ are independently selected from the group consisting of a hydrogen atom; a halogen atom; $C_1$-$C_5$-alkyl; and $C_1$-$C_5$-halogenoalkyl comprising up to 5 halogen atoms which can be the same or different;

a heterocycle of formula (A⁸)

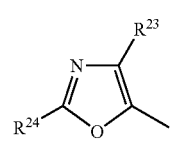

wherein:
- $R^{23}$ is selected from the group consisting of a hydrogen atom; a halogen atom; $C_1$-$C_5$-alkyl; and $C_1$-$C_5$-halogenoalkyl comprising up to 5 halogen atoms which can be the same or different; and
- $R^{24}$ is selected from the group consisting of a hydrogen atom and $C_1$-$C_5$-alkyl;

a heterocycle of formula (A⁹)

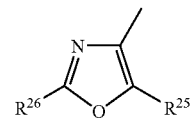

wherein:
- $R^{25}$ is selected from the group consisting of a halogen atom; $C_1$-$C_5$-alkyl; and $C_1$-$C_5$-halogenoalkyl comprising up to 5 halogen atoms which can be the same or different; and
- $R^{26}$ is selected from the group consisting of a hydrogen atom and $C_1$-$C_5$-alkyl;

a heterocycle of formula (A¹⁰)

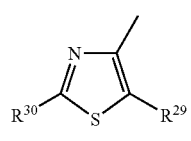

wherein:
- $R^{27}$ is selected from the group consisting of a halogen atom; $C_1$-$C_5$-alkyl; and $C_1$-$C_5$-halogenoalkyl comprising up to 5 halogen atoms which can be the same or different; and
- $R^{28}$ is selected from the group consisting of a hydrogen atom; a halogen atom; an amino; $C_1$-$C_5$-alkyl; $C_1$-$C_5$halogenoalkyl comprising up to 5 halogen atoms which can be the same or different; and a phenyl substituted by a halogen atom or by a $C_1$-$C_5$-alkyl;

a heterocycle of formula (A¹¹)

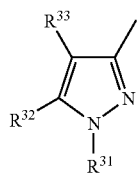

wherein:
- $R^{29}$ is selected from the group consisting of a hydrogen atom; a halogen atom; $C_1$-$C_5$-alkyl; and $C_1$-$C_5$-halogenoalkyl comprising up to 5 halogen atoms which can be the same or different; and
- $R^{30}$ is selected from the group consisting of a hydrogen atom; a halogen atom; $C_1$-$C_5$-alkyl; $C_1$-$C_5$-halogenoalkyl comprising up to 5 halogen atoms which can be the same or different; an amino; $C_1$-$C_5$-alkylamino; and di-$C_1$-$C_5$-alkylamino;

a heterocycle of formula (A¹²)

wherein:
- $R^{31}$ is selected from the group consisting of a hydrogen atom; a halogen atom; $C_1$-$C_5$-alkyl; and a phenyl substituted by a halogen atom or by a $C_1$-$C_5$-alkyl;
- $R^{32}$ is selected from the group consisting of a hydrogen atom; a halogen atom; $C_1$-$C_5$-alkyl; and $C_1$-$C_5$-halogenoalkyl comprising up to 5 halogen atoms which can be the same or different; and
- $R^{33}$ is selected from the group consisting of a hydrogen atom; a halogen atom; a nitro; and $C_1$-$C_5$-halogenoalkyl comprising up to 5 halogen atoms which can be the same or different;

a heterocycle of formula ($A^{13}$)

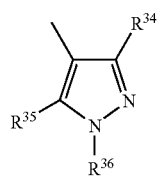

wherein:
- $R^{34}$ is selected from the group consisting of a hydrogen atom; a halogen atom; $C_1$-$C_5$-alkyl; $C_3$-$C_5$-cycloalkyl; $C_1$-$C_5$-halogenoalkyl comprising up to 5 halogen atoms which can be the same or different; $C_1$-$C_5$-alkoxy; $C_2$-$C_5$-alkynyloxy; $C_1$-$C_5$-halogenoalkoky comprising up to 5 halogen atoms which can be different; and a phenyl substituted by a halogen atom or by a $C_1$-$C_5$-alkyl;
- $R^{35}$ is selected from the group consisting of a hydrogen atom; a halogen atom; $C_1$-$C_5$-alkyl; a cyano; $C_1$-$C_5$-alkoxy; $C_1$-$C_5$-alkylthio; $C_1$-$C_5$-halogenoalkyl comprising up to 5 halogen atoms which can be the same or different; $C_1$-$C_5$-halogenoalkoxy comprising up to 5 halogen atoms which can be the same or different; an amino; $C_1$-$C_5$-alkylamino; and di($C_1$-$C_5$-alkyl); and
- $R^{36}$ is selected from the group consisting of a hydrogen atom; $C_1$-$C_5$-alkyl; and a phenyl substituted by a halogen atom or by a $C_1$-$C_5$-alkyl;

a heterocycle of formula ($A^{14}$)

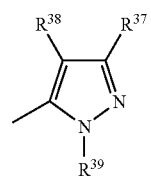

wherein:
- $R^{37}$ and $R^{38}$ are independently selected from the group consisting of a hydrogen atom; a halogen atom; $C_1$-$C_5$-alkyl; $C_1$-$C_5$-halogenoalkyl comprising up to 5 halogen atoms which can be the same or different; $C_1$-$C_5$-alkoxy; and a $C_1$-$C_5$-alkylthio; and
- $R^{39}$ is selected from the group consisting of a hydrogen atom; $C_1$-$C_5$-alkyl; and a phenyl substituted by a halogen atom or by a $C_1$-$C_5$-alkyl;

a heterocycle of formula ($A^{15}$)

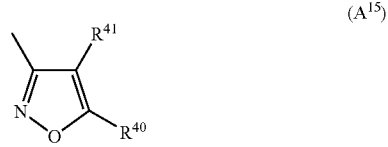

wherein:
- $R^{40}$ and $R^{41}$ are independently selected from the group consisting of a hydrogen atom; a halogen atom; $C_1$-$C_5$-alkyl; and $C_1$-$C_5$-halogenoalkyl comprising up to 5 halogen atoms which can be the same or different;

a heterocycle of formula ($A^{16}$)

wherein:
- $R^{42}$ and $R^{43}$ are independently selected from the group consisting of a hydrogen atom; $C_1$-$C_5$-alkyl; $C_1$-$C_5$-halogenoalkyl comprising up to 5 halogen atoms which can be the same or different; an amino; and a phenyl substituted by a halogen atom or by a $C_1$-$C_5$-alkyl;

a heterocycle of formula ($A^{17}$)

wherein:
- $R^{44}$ and $R^{45}$ are independently selected from the group consisting of a hydrogen atom; a halogen atom; $C_1$-$C_5$-alkyl; and $C_1$-$C_5$-halogenoalkyl comprising up to 5 halogen atoms which can be the same or different;

a heterocycle of formula ($A^{18}$)

wherein:
- $R^{46}$ is selected from the group consisting of a hydrogen atom; $C_1$-$C_5$-alkyl; $C_1$-$C_5$-halogenoalkyl comprising up to 5 halogen atoms which can be the same or different; and $C_1$-$C_5$-alkylsulfanyl; and
- $R^{47}$ is selected from the group consisting of a hydrogen atom; a halogen atom; and $C_1$-$C_5$-alkyl;

a heterocycle of formula (A$^{19}$)

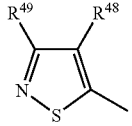
(A$^{19}$)

wherein:
R$^{48}$ and R$^{49}$ are independently selected from the group consisting of a hydrogen atom; a halogen atom; C$_1$-C$_5$-alkyl; and C$_1$-C$_5$-halogenoalkyl comprising up to 5 halogen atoms which can be the same or different; and a heterocycle of formula (A$^{20}$)

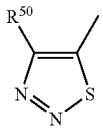
(A$^{20}$)

wherein:
R$^{50}$ is selected from the group consisting of a halogen atom; C$_1$-C$_5$-alkyl; and C$_1$-C$_5$-halogenoalkyl comprising up to 5 halogen atoms which can be the same or different;
Z$^1$ and Z$^2$ are independently selected from the group consisting of a hydrogen atom; C$_1$-C$_5$-alkyl; C$_2$-C$_5$-alkenyl; C$_2$-C$_5$-alkynyl; cyano; nitro; a halogen atom; C$_1$-C$_5$-alkoxy; C$_2$-C$_5$-alkenyloxy; C$_2$-C$_5$-alkynyloxy; C$_3$-C$_7$-cycloalkyl; C$_1$-C$_5$-alkylsulfenyl; an amino; C$_1$-C$_5$-alkylamino; di-C$_1$-C$_5$-alkylamino; C$_1$-C$_5$-alkoxycarbonyl; C$_1$-C$_5$-alkylcarbamoyl; di-C$_1$-C$_5$-alkylcarbamoyl; and N—C$_1$-C$_5$-alkyl-C$_1$-C$_5$-alkoxycarbamoyl; or
Z$^1$ and Z$^2$ together with the carbon atom to which they are bonded can form a 3-, 4-, 5- or 6-membered carbo- or heterocyclic ring, which can be substituted;
Y is a C$_1$-C$_5$-halogenoalkyl comprising up to 5 halogen atoms which can be the same or different; and
X is selected from the group consisting of a halogen atom; nitro; cyano; hydroxyl; a carboxyl group; C$_1$-C$_8$-alkyl; C$_1$-C$_6$-halogenoalkyl comprising up to 5 halogen atoms which can be the same or different; C$_1$-C$_9$-alkylamino; di-C$_1$-C$_8$-alkylamino; C$_1$-C$_8$-alkoxy; C$_1$-C$_6$-halogenoalkoxy comprising up to 5 halogen atoms which can be the same or different; C$_1$-C$_8$-alkylthio; C$_1$-C$_6$-halogenoalkylthio comprising up to 5 halogen atoms which can be the same or different; C$_2$-C$_8$-alkenyloxy; C$_2$-C$_8$-halogenoalkenyloxy comprising up to 5 halogen atoms which can be the same or different; C$_3$-C$_8$-alkynyloxy; C$_3$-C$_8$-halogenoalkynyloxy comprising up to 5 halogen atoms which can be the same or different; C$_3$-C$_8$-cycloalkyl; C$_1$-C$_8$-alkoxycarbonyl; C$_1$-C$_8$-alkylsulfinyl; C$_1$-C$_8$-alkylsulfonyl; C$_1$-C$_8$-halogenoalkylsulfinyl comprising up to 5 halogen atoms which can be the same or different;
C$_1$-C$_8$-halogenoalkylsulfonyl comprising up to 5 halogen atoms which can be the same or different, and C$_1$-C$_6$-alkoximino-C$_1$-C$_6$-alkyl;
as well as any salt or optically active isomer thereof.
8. The compound 7 wherein A is selected from the group consisting of:

a heterocycle of formula (A$^{13}$)

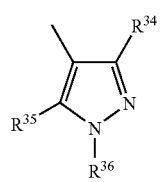
(A$^{13}$)

wherein
R$^{34}$ is selected from the group consisting of a hydrogen atom; a halogen atom; C$_1$-C$_5$-alkyl; C$_3$-C$_5$-cycloalkyl; C$_1$-C$_5$-halogenoalkyl comprising up to 5 halogen atoms which can be the same or different; C$_1$-C$_5$-alkoxy; C$_1$-C$_5$-alkynyloxy; C$_1$-C$_5$-halogenoalkoxy comprising up to 5 halogen atoms which can be the same or different; and a phenyl substituted by a halogen atom or by a C$_1$-C$_5$-alkyl;
R$^{35}$ is selected from the group consisting of a hydrogen atom; a halogen atom; C$_1$-C$_5$-alkyl; a cyano; C$_1$-C$_5$-alkoxy; C$_1$-C$_5$-alkylthio; C$_1$-C$_5$-halogenoalkyl comprising up to 5 halogen atoms which can be the same or different; C$_4$-C$_5$-halogenoalkoxy comprising up to 5 halogen atoms which can be the same or different; an amino; C$_1$-C$_5$-alkylamino; and di(C$_1$-C$_5$-alkyl); and
R$^{36}$ is selected from the group consisting of a hydrogen atom; C$_1$-C$_5$-alkyl; and a phenyl substituted by a halogen atom or by a C$_1$-C$_5$-alkyl;
and a 5-membered heterocycle that is substituted in position ortho.

9. The compound of claim 7 wherein X is selected from the group consisting of a halogen atom; C$_1$-C$_8$-alkyl; C$_1$-C$_6$-halogenoalkyl comprising up to 5 halogen atoms which can be the same or different; C$_1$-C$_8$-alkoxy; and C$_1$-C$_6$-halogenoalkoxy comprising up to 5 halogen atoms which can be the same or different.

10. The compound of claim 8 wherein X is selected from the group consisting of a halogen atom; C$_1$-C$_8$-alkyl; C$_1$-C$_6$-halogenoalkyl comprising up to 5 halogen atoms which can be the same or different; C$_1$-C$_8$-alkoxy; and C$_1$-C$_6$-halogenoalkoxy comprising up to 5 halogen atoms which can be the same or different.

11. The compound of claim 7 wherein Y is trifluoromethyl.
12. The compound of claim 8 wherein Y is trifluoromethyl.
13. The compound of claim 9 wherein Y is trifluoromethyl.
14. The compound of claim 10 wherein Y is trifluoromethyl.
15. A compound having the structural formula:

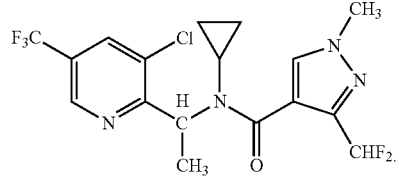

16. A method for combating phytopathogenic fungi at a locus infested or liable to be infested therewith comprising applying the compound of claim 1 to said locus.

17. A method for combating phytopathogenic fungi at a locus infested or liable to be infested therewith comprising applying the compound of claim 7 to said locus.

18. A method for combating phytopathogenic fungi at a locus infested or liable to be infested therewith comprising applying the compound of claim 15 to said locus.

* * * * *